US009155707B2

(12) United States Patent
Ying et al.

(10) Patent No.: US 9,155,707 B2

(45) Date of Patent: Oct. 13, 2015

(54) CORE-SHELL MICROSPHERES

(75) Inventors: Jackie Y. Ying, Singapore (SG); Shona Pek, Singapore (SG); Pemakorn Pitukmanorom, Singapore (SG); Siti Thaharah Mohamed, Singapore (SG)

(73) Assignee: Agency for Science, Technology and Research, Singapore (SG)

(*) Notice: Subject to any disclaimer, the term of this patent is extended or adjusted under 35 U.S.C. 154(b) by 73 days.

(21) Appl. No.: 14/123,935

(22) PCT Filed: Jun. 8, 2012

(86) PCT No.: PCT/SG2012/000208

§ 371 (c)(1), (2), (4) Date: Mar. 24, 2014

(87) PCT Pub. No.: WO2012/169972

PCT Pub. Date: Dec. 13, 2012

(65) Prior Publication Data

US 2014/0199381 A1 Jul. 17, 2014

Related U.S. Application Data

(60) Provisional application No. 61/495,328, filed on Jun. 9, 2011.

(51) Int. Cl.

| | |
|---|---|
| ***A61K 9/48*** | (2006.01) |
| ***A61K 31/435*** | (2006.01) |
| ***A61K 47/34*** | (2006.01) |
| ***C08J 3/02*** | (2006.01) |
| ***C08L 87/00*** | (2006.01) |
| ***C08J 3/12*** | (2006.01) |

(52) U.S. Cl.

CPC ................. *A61K 9/48* (2013.01); *A61K 31/435* (2013.01); *A61K 47/34* (2013.01); *C08J 3/02* (2013.01); *C08J 3/126* (2013.01); *C08L 87/00* (2013.01); *C08J 2387/00* (2013.01)

(58) Field of Classification Search

None

See application file for complete search history.

(56) References Cited

U.S. PATENT DOCUMENTS

| | | | |
|---|---|---|---|
| 7,589,057 | B2 | 9/2009 | Chang et al. |
| 2008/0299178 | A1 | 12/2008 | Burke et al. |

FOREIGN PATENT DOCUMENTS

| | | |
|---|---|---|
| CN | 101461786 | 6/2009 |
| WO | WO 2012/034049 A2 | 3/2012 |

OTHER PUBLICATIONS

Bertram et al., Sustained delivery of timolol maleate from poly(lactic-co-glycolic acid)/poly(lactic acid) microspheres for over 3 months. J Microencapsul. Feb. 2009;26(1):18-26. Erratum in: J Microencapsul. Feb. 2009;26(1):26.

Cui et al., Preparation and characterization of melittin-loaded poly (DL-lactic acid) or poly (DL-lactic-co-glycolic acid) microspheres made by the double emulsion method. J Control Release. Oct. 3, 2005;107(2):310-9.

Lee et al., Double-walled microspheres for the sustained release of a highly water soluble drug: characterization and irradiation studies. J Control Release. Oct. 30, 2002;83(3):437-52.

Lu et al., Synthetic Bone Substitutes. Curr Opin in Orthopedics. 2000;11:383-90.

Pollauf et al., Small-molecule release from poly(D,L-lactide)/poly(D,L-lactide-co-glycolide) composite microparticles. J Pharm Sci. Sep. 2005;94(9):2013-22.

Ranganath et al., Hydrogel matrix entrapping PLGA-paclitaxel microspheres: drug delivery with near zero-order release and implantability advantages for malignant brain tumour chemotherapy. Pharm Res. Sep. 2009 ;26(9):2101-14. Epub Jun. 20, 2009.

Sirsi et al., Formulation of polylactide-co-glycolic acid nanospheres for encapsulation and sustained release of poly(ethylene imine)-poly(ethylene glycol) copolymers complexed to oligonucleotides. J Nanobiotechnology. Apr. 7, 2009;7:1.

Tan et al., Fabrication of double-walled microspheres for the sustained release of doxorubicin. J Colloid Interface Sci. Nov. 1, 2005;291(1):135-43. Epub Jun. 17, 2005.

*Primary Examiner* — Amber D Steele
*Assistant Examiner* — Schuyler Milton
(74) *Attorney, Agent, or Firm* — Wolf, Greenfield & Sacks, P.C.

(57) ABSTRACT

The specification describes a substance comprising a plurality of microparticles. The microparticles comprise a core comprising a first polymer and a shell surrounding said core and comprising the first polymer and a second polymer, wherein the second polymer is less rapidly degradable than the first polymer. A process for making the microparticles and uses of the microparticles are also described.

20 Claims, 9 Drawing Sheets a)

b)

a)

b)

CORE-SHELL MICROSPHERES

RELATED APPLICATIONS

This application is a national stage filing under 35 U.S.C. §371 of International application number PCT/SG2012/000208, filed Jun. 8, 2012, and which claims priority under 35 U.S.C. §119from U.S. provisional application serial number 61/495,328, filed Jun. 9, 2011, the entire contents of each of which are incorporated by reference herein.

FIELD

The invention relates to core-shell microspheres, processes for making them and uses thereof. This application claims priority from U.S. provisional application number61/495, 328, the entire contents of which are incorporated herein by cross-reference.

BACKGROUND

In many applications there is a need for controlled release of a substance to a medium. This need has in the past been addressed by encapsulating the substance in particles which release the substance over time. It has been a challenge to accurately control the rate of release of the substance to the medium. A further challenge is to introduce a delay period for release of the substance. Such a delay period may, for example, be desirable in cases where some time is required for the particles containing the substance to reach their desired destination in order to release the substance in the most effective location. Such a delay may also be desirable for the sequential delivery of multiple active substances each at different timepoints in the patient's treatment regime, or for cyclic delivery of multiple different hormones.

The present invention is designed to at least partially satisfy the above stated needs.

SUMMARY OF INVENTION

Aspects of the invention are as set out below.

A substance comprising a plurality of microparticles, said microparticles comprising a core comprising a first polymer and a shell surrounding said core and comprising the first polymer and a second polymer, said second polymer being less rapidly degradable than the first polymer. The first polymer in the shell may be in the form of continuous pathways passing through said shell.

The substance wherein the second polymer is less rapidly biodegradable than the first polymer.

The substance wherein the second polymer is semicrystalline.

The substance wherein the second polymer has a molecular weight of about 100 kDa.

The substance wherein the second polymer has a molecular weight of more than 100 kDa.

The substance wherein the second polymer has a molecular weight of more than about 160 kDa.

The substance of wherein the first polymer has a molecular weight of about 1 to about 60 kDa, for example about 7 to about 24 kDa.

The substance wherein the first polymer has a molecular weight of greater than about 75 kDa.

The substance wherein the weight ratio of the second polymer to the first polymer in the microparticles is within the range of about 1:1.25 to about 2:1.

The substance wherein the weight ratio of the second polymer to the first polymer in the microparticles is within the range of about 1:1 to about 1:1.25.

The substance wherein degradation of the first polymer produces no toxic products.

The substance wherein the first polymer is poly(D,L-lactic-co-glycolic acid) (PLGA) and the second polymer is poly (L-lactic acid) (PLLA).

The substance wherein the first polymer is present in the shell at less than about 25 wt %.

The substance wherein the first and second polymers are at least partially immiscible, optionally substantially immiscible.

The substance wherein the first polymer forms (or is in the form of) a plurality of continuous pathways or channels through the shell.

The substance wherein the core comprises a releasable material.

The substance wherein the releasable material is in particulate form.

The substance wherein the releasable material is adsorbed onto, or absorbed into, or both adsorbed onto and absorbed into, nanoparticles in the core.

The substance wherein the nanoparticles are inorganic nanoparticles.

The substance wherein the nanoparticles comprise apatite.

The substance wherein the first and second polymers are substantially immiscible and the first polymer forms a plurality of continuous pathways through the shell and wherein the nanoparticles, if present, or the particles of the releasable material, if present, are smaller than the diameter of the pathways.

The substance wherein the releasable material is a therapeutic substance.

The substance wherein the therapeutic substance is a drug.

The substance wherein the releasable material is selected from the group consisting of a protein, a protein fragment, an enzyme, DNA, a DNA fragment, RNA, an RNA fragment, a polysaccharide, a hormone, a growth factor, a drug which is none of the above and mixtures of any two or more of these.

The substance wherein the releasable material is hydrophilic.

The substance wherein the releasable material is dispersible in, or soluble in, water.

The substance wherein the releasable material is hydrophobic.

The substance wherein the releasable material is substantially insoluble in water.

The substance wherein the microparticles are dispersed in a carrier.

The substance wherein the carrier is a hydrogel, a membrane or a scaffold.

The substance wherein the microparticles are at least partially adhered together to form a solid mass.

A process for making a substance comprising a plurality of microparticles, optionally for making the substance of any one of paragraphs to, said process comprising: combining a first solution comprising a first polymer in a first solvent, and a second solution comprising a second polymer in a second solvent, to form a mixed polymer solution, said second polymer being less rapidly degradable than the first polymer and the first and second polymers being at least partially immiscible, optionally substantially immiscible, and said first and second solvents being miscible with each other; emulsifying the mixed polymer solution in an aqueous medium to form an emulsion, said aqueous medium being at least partially immiscible with the first and second solvents; aging the emulsion for sufficient time to allow for at least partial separation of the first polymer and the second polymer within droplets of the emulsion so as to form a core comprising the first polymer and a shell surrounding the core and comprising the first polymer and the second polymer; and removing the first and second solvents to form the substance as an aqueous suspension, wherein the microparticles each comprise a core comprising the first polymer and a shell surrounding said core and comprising the first polymer and the second polymer.

The process wherein the first and second solvents are the same.

The process wherein the aqueous medium is at least partially saturated with the first solvent and/or the second solvent.

The process wherein the aqueous medium comprises an emulsifying agent.

The process wherein the emulsifying agent is methylcellulose.

The process wherein the first solution comprises a releasable material, whereby the cores of the microparticles contain said releasable material.

The process wherein the releasable material is in particulate form.

The process wherein the releasable material is adsorbed onto, or absorbed into, or both adsorbed onto and absorbed into, nanoparticles.

The process comprising the step of preparing the first solution by combining a precursor solution with the releasable material, said precursor solution comprising the first polymer in the first solvent.

The process wherein the weight ratio of releasable material to first polymer is less than 1:1.

The process wherein the second polymer is semicrystalline.

The process wherein the second polymer has a molecular weight of about 100 kDa.

The process wherein the second polymer has a molecular weight of more than 100 kDa.

The process wherein the second polymer has a molecular weight of more than about 160 kDa.

The process wherein the first polymer has a molecular weight of less than about 40 kDa, optionally of less than about 35 kDa, optionally of about 1 to about 40 kDa, optionally of about 3 to 24 kDa, optionally of about 7 to about 24 kDa.

The process wherein the first polymer has a molecular weight of greater than about 75 kDa.

The process wherein the weight ratio of the second polymer to the first polymer in the mixed polymer solution is such that the process forms microparticles comprising a core comprising the first polymer and a shell surrounding said core and comprising the first polymer and the second polymer.

The process wherein the weight ratio of the second polymer to the first polymer in the mixed polymer solution is within the range of about 1:1.25 to about 2:1.

The process wherein the weight ratio of the second polymer to the first polymer in the mixed polymer solution is within the range of about 1:1 to about 1:1.25.

The process comprising the step of selecting at least one of the molecular weight of the first polymer, the molecular weight of the second polymer and the ratio of the first and second polymers so that a releasable material, if present in the cores of the microparticles, is releasable from the microparticles at a desired rate or with a desired delay period.

The process wherein degradation of the first polymer produces no toxic products.

The process wherein the first polymer is poly(D,L-lactic-co-glycolic acid) (PLGA) and the second polymer is poly(L-lactic acid) (PLLA).

The process wherein the step of aging is conducted with continuous stirring.

The process wherein the step of solvent extraction is conducted at least partially concurrently with the step of aging whereby the steps of aging and solvent extraction are for sufficient time to allow for at least partial separation of the first polymer and the second polymer within droplets of the emulsion so as to form a core comprising the first polymer and a shell surrounding the core and comprising the first polymer and the second polymer.

The process wherein the first and second solvents are partially miscible with the aqueous liquid and the step of removing the solvent(s) comprises diluting the particulate substance as aqueous suspension with the aqueous liquid which has neither the first nor the second solvent therein.

The process comprising separating the particulate substance from the aqueous liquid.

The process comprising heating the separated particulate substance in a mould for sufficient time and at sufficient temperature to cause the microparticles to adhere together so as to form pellets of the particulate substance.

The process wherein the sufficient temperature is the glass transition temperature of the second polymer.

The process wherein the first solution comprises a releasable material and the sufficient temperature is below the temperature at which said releasable material degrades over the sufficient time.

A method for delivering a material to a liquid comprising exposing a substance according to said liquid in the presence of a degrading agent which is capable of degrading the first polymer, said substance being one in which the cores of the microparticles contain the material.

The method wherein the liquid is, or comprises, the degrading agent.

The method which is for a non-therapeutic, non-diagnostic purpose.

The method wherein the material is a therapeutic substance and the liquid is a bodily fluid, whereby the method is for delivering the therapeutic substance to a patient.

The method wherein the patient is a non-human.

The method wherein the microparticles of the substance are adhered together.

Use of a substance for the treatment of a condition in a patient, optionally a non-human patient, wherein the releasable material is indicated for treatment of said condition.

Use, wherein the condition is pain and the releasable material is an analgesic.

Use of a substance wherein the condition is glaucoma, wherein the releasable material is indicated for treatment of glaucoma.

Use wherein the releasable material is brimonidine tartarate.

Use wherein the releasable material is an antifibrotic agent.

Use wherein the antifibrotic agent is fluorouracil.

A composite substance comprising at least two different substances, each of said substances being a substance, wherein: the cores of the microparticles of each of the substances comprises a releasable material; and the shells of the microparticles of the different substances are such that they degrade over different times under the same conditions, whereby the releasable materials of in the microparticles of the different substances are capable of releasing sequentially.

The composite substance of wherein the releasable material of at least two of the different substances are the same.

The composite substance wherein the releasable material of each of the different substances is different from the releasable material of each of the other different substances.

The composite substance wherein the shells of the microparticles of the different substances are of different thicknesses so that that they degrade over different times under the same conditions.

The composite substance wherein the molecular weight of the second polymer of the microparticles of the different substances is different so that the shells of the different substances degrade over different times under the same conditions.

The composite substance wherein the first polymer of the microparticles of each of the different substances is the same and the second polymer of the microparticles of each of the different substances is the same.

The composite substance wherein the first polymer is poly (D,L-lactic-co-glycolic acid) (PLGA) and the second polymer is poly(L-lactic acid) (PLLA).

Some particular embodiments of the invention are set out below.

A substance comprising a plurality of microparticles, said microparticles comprising a core comprising poly(D,L-lactic-co-glycolic acid) (PLGA) and a shell surrounding said core and comprising PLGA and poly(L-lactic acid) (PLLA), wherein the core comprises a releasable material. The PLGA in the shell may be in the form of channels passing through said shell.

A substance comprising a plurality of microparticles, said microparticles comprising a core comprising poly(D,L-lactic-co-glycolic acid) (PLGA) and a shell surrounding said core and comprising PLGA and poly(L-lactic acid) (PLLA), wherein the core comprises a releasable material, said releasable material being in particulate form or being adsorbed onto, or absorbed into, or both adsorbed onto and absorbed into, inorganic nanoparticles in the core. The PLGA in the shell may be in the form of channels passing through said shell.

A composite substance comprising at least two different substances, each of said substances comprising a plurality of microparticles, said microparticles comprising a core comprising poly(D,L-lactic-co-glycolic acid) (PLGA) and a shell surrounding said core and comprising PLGA and poly(L-lactic acid) (PLLA), wherein the core comprises a releasable material, wherein the shells of the microparticles of the different substances are such that they degrade over different times under the same conditions, whereby the releasable materials of in the microparticles of the different substances are capable of releasing sequentially.

A process for making a substance comprising a plurality of microparticles, said process comprising: combining a first solution comprising poly(D,L-lactic-co-glycolic acid) (PLGA) in DCM (dichloromethane), or other suitable solvent such as DMF (dimethylformamide), DMSO (dimethyl sulfoxide), methanol or a mixture of any one or more of these with DCM, and a second solution comprising poly(L-lactic acid) (PLLA) in DCM or other suitable solvent such as DMF, DMSO, methanol or a mixture of any one or more of these with DCM, to form a mixed polymer solution; emulsifying the mixed polymer solution in an aqueous medium to form an emulsion, said aqueous medium being at least partially immiscible with the first and second solvents; aging the emulsion for sufficient time to allow for at least partial separation of the PLGA and the PLLA within droplets of the emulsion so as to form a core comprising PLGA and a shell surrounding the core and comprising PLGA and PLLA; and removing the DCM to form the substance as an aqueous suspension, wherein the microparticles each comprise a core comprising PLGA and a shell surrounding said core and comprising PLGA and PLLA.

A process for making a substance comprising a plurality of microparticles, said process comprising: combining a first solution comprising poly(D,L-lactic-co-glycolic acid) (PLGA) and a releasable material, said releasable material being in particulate form or being adsorbed onto, or absorbed into, or both adsorbed onto and absorbed into, inorganic nanoparticles, in DCM (dichloromethane), and a second solution comprising poly(L-lactic acid) (PLLA) in DCM, to form a mixed polymer solution; emulsifying the mixed polymer solution in an aqueous medium to form an emulsion, said aqueous medium being at least partially immiscible with the first and second solvents; aging the emulsion for sufficient time to allow for at least partial separation of the PLGA and the PLLA within droplets of the emulsion so as to form a core comprising PLGA and a shell surrounding the core and comprising PLGA and PLLA; and removing the DCM to form the substance as an aqueous suspension, wherein the microparticles each comprise a core comprising PLGA and a shell surrounding said core and comprising PLGA and PLLA, said core comprising the releasable material, said releasable material being in particulate form or being adsorbed onto, or absorbed into, or both adsorbed onto and absorbed into, inorganic nanoparticles in the core.

BRIEF DESCRIPTION OF DRAWINGS

In FIG. 2 the order of the curves, from the bottom, is 30 mg, 60 mg, 90 mg, 120 mg for the left hand graph and 5 mg, 15 mg, 30 mg and 60 mg for the right hand graph.

In FIG. 12*a*, the order of curves, from the bottom, is 30, 60, 90, 120 mg and in FIG. 12*b*, the order of curves, from the bottom, is 5, 15, 30 and 60 mg.

In FIG. 13*a*, the order of curves, from the bottom, is 30, 60, 90, 120 mg and in FIG. 13*b*, the order of curves, from the bottom, is 30, 60 and 90 mg, with 120 mg almost superposed on 90 mg.

DESCRIPTION OF EMBODIMENTS

Figure 1:
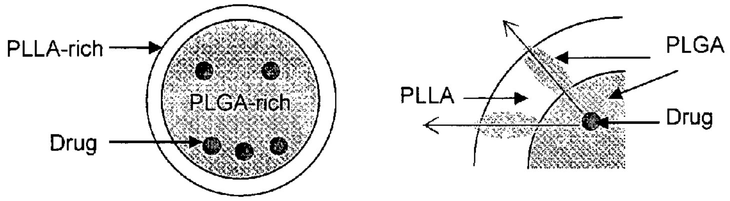
FIG. 1 is diagram illustrating a postulated mechanism of, drug release.

The present invention relates to core-shell polymer/polymer-inorganic microspheres for tunable delayed release of for example, drugs, proteins and active ingredients. This technology provides a method for preparing microspheres that can release substances such as drugs, proteins and/or active ingredients with a delayed profile. With this technology, it is possible to specify a lag time before substances are released at a constant rate. Long-term sustained release is therefore possible by combining batches of microspheres with different lag times, such that when a drug, protein or active ingredient has been completely (or partially) released from a particular batch of microspheres, there will be another batch of microspheres ready to start releasing this or another drug, protein or active ingredient.

These microspheres may also be incorporated into a carrier, such as a hydrogel, a membrane or a scaffold for ease of implantation at the desired release site. This carrier can be replaced when all the drug, protein or active ingredient has been released.

It is well known that different polymers are generally not fully miscible with each other (see for example Kim, J. H. et al, *Macromolecules* 2006, 39, 1297-1299, page 1297). Thus mixes of polymers commonly phase separate. In the present instance, two dissimilar polymers are combined in solution in the droplets of an emulsion. Initial phase separation provides two concentric phases, the inner (which becomes the core) being rich in a first polymer and the outer (which becomes the shell) being rich in a second polymer. As further phase separation occurs, it is thought that the outer phase forms into a matrix of the second polymer having channels or pathways of the first polymer within or through the matrix of the second polymer. Once the solvent is withdrawn, or at least partially withdrawn from the droplets, these phases solidify so as to form the final particles and "freeze in" the final structure.

If the first polymer is provided, e.g. loaded or combined, with a releasable material, for example an active compound such as a drug, a layered particle may be formed in which the releasable material is located in the core of the particle. Degradation of the first polymer by placing the particle in an environment capable of degrading said first polymer is then thought to open up channels through the shell through which the releasable material may be released.

In this context, the term "degradation" and related terms should be taken in their broadest sense. Thus this term may refer to a process by which the first process is rendered mobile or is converted to a mobile species. This may include depolymerisation or partial depolymerisation, dissolution, chemical decomposition or some other process. The degradation is in respect of, commonly initiated by, an environment in which the particles are used or are intended to be used. Thus if the particles are to release a releasable material into an industrial liquid, the first polymer may be degradable by that liquid, or by a component thereof. For example the first polymer may be degradable in an acidic environment if the releasable material is to be released into an acidic environment. This may for example be useful if the releasable material is a base, so that the particles may be used to prevent excessive acidification. In another example the first polymer may be biodegradable if the releasable material is to be released in a biological fluid, e.g. in vivo. In a further example the first polymer may be photodegradable, and release of the releasable material may be promoted by irradiation of a suspension of the particles. The irradiation may be at a wavelength specifically suited for degradation of the first polymer. Thus the invention provides in a particular embodiment a substance comprising a plurality of microparticles for release of a releasable material into an environment, said microparticles comprising a core comprising the releasable material dispersed in a first polymer and a shell surrounding said core and comprising the first polymer and a second polymer, said first polymer being degradable in said environment and second polymer being less rapidly degradable in said environment than the first polymer and the first polymer forming continuous pathways through the second polymer in the shell.

In the microparticles of the invention, the first polymer may form (or may be in the form of) a plurality of continuous pathways or channels through the shell. The first polymer may be disposed within the shell such that, once removed (e.g. by degradation) it exposes a plurality of continuous pathways or channels through the shell. The pathways or channels (either of the first polymer or as exposed by removal thereof) may be in the form of a network of interconnected pathways or channels, or may form discrete pathways or channels between an outside surface of the shell and an inside surface of the shell. The channels or passages exposed by removal of the first polymer may be such that they permit passage of a fluid between an outside surface of the shell and an inside surface of the shell. The shell may therefore be in the form of an interpenetrating network of the first polymer and the second polymer.

Whereas one application envisaged for this invention is the release of therapeutic or diagnostic substances to a patient, other non-therapeutic and/or non-diagnostic uses are also envisaged, for example release of brightening agents in clothes washing, release of catalysts/enzymes in industrial processes etc. Even in the event that a therapeutic or diagnostic application is used, the patient may be a non-human patient, e.g. a mammal, vertebrate, bird, fish, domestic animal (e.g. cow, horse, dog, cat, sheep, pig etc.) or some other type of non-human patient. In some applications the patient is a human patient. In cases where the particles are used in vivo, it is preferred that neither the first nor the second polymer nor any biodegradation products of either of them is toxic or otherwise harmful to the organism in which the particles are used or to which they are administered. The invention may be applied in vitro. It may be applied in vivo.

As noted above, the first polymer should be more readily degraded than the second polymer. In some instances the first polymer is degradable and the second polymer is non-degradable or only very slowly degradable. In particular embodiments the first polymer is biodegradable and the second polymer is non-biodegradable or only very slowly biodegradable. Additionally, the first and second polymers are preferably not be fully miscible with each other. As noted above, this is an easy requirement to satisfy since fully miscible polymer pairs are not common. Each of the polymers may, independently, be a homopolymer or a copolymer. In the event that one is a copolymer, the main polymer chain may comprise at least two separate comonomers. In some embodiments the first polymer is a copolymer and the second polymer is a homopolymer. The monomer of the second polymer may be a comonomer of the first polymer. In such cases, an (or the) other comonomer of the first polymer may introduce increased degradability to the copolymer. This may be by virtue of being itself degradable (e.g. biodegradable, photodegradable etc.) or by having a degradable linkage to another comonomer.

The miscibility of the first polymer in the second polymer at the temperature at which the particles are formed (or at 15, 20, 25 or 30° C.) may be less than about 10% by weight or by volume, or less than about 5, 4, 3, 2, 1, 0.5, 0.2 or 0.1%, or may be about 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9 or 10% by weight or volume. The miscibility of the second polymer in the first polymer at the temperature at which the particles are formed may be less than about 10% by weight or by volume, or less than about 5, 4, 3, 2, 1, 0.5, 0.2 or 0.1%, or may be about 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9 or 10% by weight or volume.

The first and second polymers may be substantially immiscible at the temperature at which the particles are formed. Suitable polymers (independently the first and second polymers) for use in the present invention include condensation polymers, e.g. polyesters, polyamides, polyimides, polyanhydrides etc. In particular suitable polymers include polymers and copolymers of hydroxyfunctional carboxylic acids. These may, independently, be C2 to C6 hydroxyfunctional carboxylic acids, e.g. C2, C3, C4, C5 or C6 hydroxyfunctional carboxylic acids. They may be monocarboxylic acids. They may monohydroxyfunctional. They may primary hydroxyfunctional, or may be secondary hydroxyfunctional or may be tertiary hydroxyfunctional. It may be useful to use polymers of non-toxic monomers so as to avoid production of toxic products when degrading the polymers. A suitable first polymer is a copolymer of lactic acid (either D, L or DL) with another hydroxyacid such as glycolic acid. The first polymer may be amorphous. It may be non-crystalline. This may facilitate its degradation. Independently, the second polymer may be a polymer of a hydroxyfunctional carboxylic acid such as lactic acid (D, L or DL). A useful pair of polymers for use in the invention is poly(D,L-lactic-co-glycolic acid) as the first polymer (PLGA) and poly(L-lactic acid) (PLLA) as the second polymer. The second polymer may be semicrystalline or may be crystalline. This may inhibit its degradation. The first and second polymers may, independently, be linear. They may be uncrosslinked. In the case of copolymers, there may be at least two comonomers present in the main chain of the copolymer. Where reference is made in this specification to a monomer being present in a polymer (or related phrases), this refers to the presence of a monomer unit from that monomer being present in the polymer.

As discussed above, it is important in the present invention that the first polymer be degradable in the environment in which it is to be used. It may be non-degradable, or very slowly degradable, in other environments to which it may be exposed and in which release of the releasable material is undesirable. It may for example be non-degradable, or very slowly degradable, in neutral water, or in air. The first polymer may be such that its rate of degradation depends on its molecular weight. This enables the release of the releasable material from the particles to be controlled by the molecular weight of the first polymer. The molecular weight of the first polymer may be such as to obtain the desired release profile of the releasable material. It may be for example greater than about 1 kDa, or greater than about 2, 3, 4, 5, 7, 10, 15, 20, 30, 50, 75 or 100 kDa, or it may be less than about 40 kDa, or less than about 35, 30, 25, 20, 15 or 10 kDa, or may be between about 1 and about 100 kDa, or may be between about 1 and 60, 1 and 58, 1 and 35, 3 and 35, 5 and 35, 10 and 35, 20 and 35, 1 and 5, 1 and 10, 1 and 5, 4 and 7, 5 and 75, 5 and 50, 5 and 25, 5 and 20, 5 and 15, 5 and 10, 10 and 100, 20 and 100, 50 and 100, 10 and 50, 20 and 50, 10 and 20, 7 and 24, 7 and 15, 15 and 24 or 75 and 100 kDa, e.g. about 1, 2, 3, 4, 5, 6, 7, 8, 9, 10, 15, 20, 25, 30, 35, 40, 45, 50, 60, 70, 80, 90 or 100. The second polymer may have a high molecular weight. This may inhibit its degradation in use. It may have a molecular weight of greater than about 50 kDa, or greater than 75, 100, 125, 150 or 200 kDa, or between about 50 and about 250 kDa, or between about 50 and 200, 50 and 1050, 100 and 250 or 100 and 200 kDa, e.g. about 50, 60, 70, 80, 90, 100, 125, 150, 175, 200, 225 or 250 kDa. In some instances the second polymer may have lower molecular weight, for example as low as 2 kDA. The second polymer may have a molecular weight of from 2 to 50 kDa, or 2 to 20, 2 to 10, 10 to 50, 20 to 50, to 30 or 15 to 20 kDa, e.g. about 2, 3, 4, 5, 10, 15, 20, 25, 30, 35, 40, 45 or 50 kDa. In one example, the first polymer has a molecular weight of about 4 to about 7 kDa and the second polymer has a molecular weight of about 15 to about 20 kDa. The above molecular weights may be number average, or may be weight average, or may be viscosity average. They may be polystyrene equivalent molecular weights (i.e. measured using known molecular weight polystyrene standards) or they may be molecular weights calculated from the intrinsic viscosity using the Mark-Houwink-Sakurada equation. The first and second polymers may, independently, have a narrow or a broad molecular weight. They may, independently, have a polydispersity (defined as Mw/Mn) of less than 20 or less than 15, 10, 9, 8, 7, 6, 5, 4, 3, 2, 1.5, 1.4, 1.3, 1.2 or 1.1, or of about 1 to 20, 1 to 10, 1 to 5, 1 to 2, 1 to 1.5, 1 to 1.2, 2 to 20, 5, to 20, 10 to 20, 15 to 20, 2 to 10, 2 to 5 or 5 to 10, e.g. of about 1, 1.1, 1.2, 1.3, 1.4, 1.5, 2, 3, 4, 5, 6, 7, 8, 9, 10, 15 or 20, although in some cases polymers with polydispersities of greater than 20 may be used.

The molecular weights of the first polymer and second polymer may be chosen such that the core degrades faster relative to the shell, i.e. that the first polymer degrades faster than the second polymer. The second polymer should be slower degrading relative to the first polymer under the conditions of use. Thus if the first polymer in the core has very low molecular weight and degrades very quickly, it is possible to use a quite low molecular weight second polymer for the shell. It is preferred that in use the shell remain intact for the duration of release of the releasable material and for the degradation time of the core. In some applications, it may desirable for the shell to degrade completely soon after the drug is completely released. In such a situation, the second polymer in the shell should be chosen to have as low a molecular weight as possible for early degradation after complete drug release, while still remaining intact during the time the drug is being released.

In an example, a 2 kDa PLLA was used as the second polymer in the shell, paired with a PLGA first polymer in the core having molecular weight less than 7 kDa. It was found that PLGA of molecular weight 7 kDa degraded significantly faster than PLLA of molecular weight 2 kDa. This resulted in a drug release regime of around 10 days rather than several months when using high molecular weight PLLA/PLGA.

The second polymer may be present in greater amount (i.e. greater weight) than the first polymer. The ratio of second polymer to first polymer may be between about 1 and about 5 (i.e. about 1:1 and about 5:1), or about 1 to 4, 1, to 3, 1 to 2, 2 to 3, 1 to 1.5, 1.5 to 2, 1 to 1.25, 1.25 to 2, 1.25 to 1.5, 1.5 to 2 or 1.5 to 1.75, e.g. about 1, 1.05, 1.1, 1.15, 1.2, 1.25, 1.3, 1.35, 1.4, 1.45, 1.5, 1.6, 1.7, 1.75, 1.8, 1.9, 2, 2.5, 3, 3.5, 4, 4.5 or 5.

The shell of the particles may comprise less than about 25% by weight or volume of the first polymer, or less than about 20, 15 or 10%, or may comprise between about 5 and about 25% of the first polymer, or between about 10 and 25, 15 and 25, 20 and 25, 5 and 15 or 15 and 20%, e.g. about 5, 10, 15, 20 or 25% thereof. This proportion may approximately equate to the proportion of pore volume in the shell once the first polymer has degraded in use.

The microparticles of the invention may be between about 0.5 and about 1000 microns, or between about 0.5 and about 500 microns in diameter, or between about 0.5 and 200, 0.5 and 100, 0.5 and 50, 0.5 and 20, 0.5 and 10, 0.5 and 5, 0.5 and 2, 0.5 and 1, 1 and 500, 2 and 500, 5 and 500, 10 and 500, 50 and 500, 100 and 500, 200 and 500, 1 and 100, 1 and 10, 10 and 100, 10 and 50 or 50 and 100 microns, e.g. about 0.5, 1, 1.5, 2, 2.5, 3, 3.5, 4, 4.5, 5, 6, 7, 8, 9, 10, 15, 20, 25, 30, 35, 40, 45, 50, 60, 70, 80, 90, 100, 150, 200, 250, 300, 350, 400, 450 or 500 microns, or even larger, e.g. 550, 600, 650, 700, 750, 800, 850, 900, 950 or 1000 microns. This may be a mean diameter. The microparticles may be essentially monodispersed or may have a range of particle sizes. The ratio of the diameter of the particles to the diameter of the core may be about 1.05 to about 5, or about 1.05 to 3, 1.05 to 2, 1.05 to 1.5, 1.1 to 5, 1.5 to 5, 2 to 5, 3 to 5, 1.5 to 2, 1.5 to 3, 1.5 to 2.5 or 1.2 to 2, e.g. about 1.05, 1.1, 1.15, 1.2, 1.25, 1.3, 1.35, 1.4, 1.45, 1.5, 1.6, 1.7, 1.8, 1.9, 2, 2.5, 3, 3.5, 4, 4.5 or 5. The core may have a diameter of from about 0.2 to about 500 microns, or about 0.5 to 500, 1 to 500, 20 to 500, 5 to 500, 10 to 500, 20 to 500, 50 to 500, 100 to 500, 200 to 500, 0.2 to 200, 0.2 to 100, 0.2 to 50, 0.2 to 20, 0.2 to 10, 0.2 to 5, 0.2 to 2, 1 to 200, 10 to 50, 10 to 100, 50 to 250, 10 to 20 or 5 to 10 microns, e.g. about 0.2, 0.3, 0.4, 0.5, 1, 2, 3, 4, 5, 6, 7, 8, 9, 10, 15, 20, 25, 30, 35, 40, 45, 50, 60, 70, 80, 90, 100, 150, 200, 250, 300, 350, 400, 450 or 500 microns. The microparticles may be spherical or approximately spherical. They may be oblate spherical, ovoid, polyhedral or some other suitable shape. They should be solid.

The releasable material may be in the core of the particles in undissolved form or it may be dissolved in the first polymer. It may be in particulate form. It may be adsorbed onto, or absorbed into, a support particle. The support particle may be an inorganic particle. The inorganic particle may be for example a salt particle, a mineral particle, a zeolite particle or some other particle. An apatite particle is a suitable example. The support particle, or the particle of the releasable material, may be a nanoparticle. It may have a diameter of about 1 to about 20 nm, or about 1 to 10, 1 to 5, 1 to 2, 2 to 20, 5 to 20, 10 to 20, 2 to 10 or 5 to 10 nm, e.g. about 1, 2, 3, 4, 5, 6, 7, 8, 9, 10, 11, 12, 13, 14, 15, 16, 17, 18, 19 or 20 nm, or may be larger (e.g. about 30, 40, 50 or 100 nm) or smaller than this. The support particle, or the particle of the releasable material, may be sufficiently small to pass through pores in the shell of the microparticles formed by degradation of the first polymer in the shell. Those pores may have a diameter of about 10 to about 1000 nm, or about 10 to 500, 10 to 200, 10 to 100, 10 to 50, 20 to 1000, 50 to 1000, 100 to 1000, 200 to 1000, 500 to 1000, 100 to 500, 50 to 200, 10 to 20, 20 to 50 or 20 to 30 nm, e.g. about 10, 15, 20, 25, 30, 35, 40, 45, 50, 60, 70, 80, 90, 100, 150, 200, 250, 300, 350, 400, 450, 500, 600, 700, 800, 900 or 1000 nm. In some instances they may be larger than this, e.g. about 1 to about 50 microns, or about 1 to 20, 1 to 10, 1 to 5, 5 to 50, 10 to 50, 20 to 50, 5 to 20, 10 to 20 or 20 to 30 microns, e.g. about 1, 2, 3, 4, 5, 6, 7, 8, 9, 10, 15, 20, 25, 30, 35, 40, 45 or 50 microns. The rate of release of the releasable material may be controlled by controlling the size of the support particles or particles of the releasable material (referred to herein as "releasable particles"). Thus the larger the releasable particles, the slower they will be released through the pores formed in the shell by degradation of the first polymer. In the extreme, if the releasable particles are larger than the pores, then the only mechanism for release is by either degradation/dissolution of the second polymer or by dissolution of the releasable particles or at least of the releasable material, followed by diffusion of the releasable material out of the pores. The acidic products of PLGA degradation may degrade the apatite core and release the adsorbed material.

The releasable material may be a protein, a protein fragment, an enzyme, DNA, a DNA fragment, RNA, an RNA fragment, a polysaccharide, a hormone, a growth factor, a corticosteroid, an antibiotic, a radiopharmaceutical, a drug which is none of the above, radiotracer, an imaging agent, a dye, a cosmeceutical agent or a mixture of any two or more of these, or may be some other substance.

The core-shell particles of the invention may be in the form of discrete particles, or may be adhered or partially adhered to each other. They may for example be sintered to form a mass of particles. This may be achieved by heating the particles to a suitable sintering temperature. This will of course depend on the nature of the second polymer. It may be above the glass transition temperature of the second polymer. It may be for example about 35 to 55° C., or about 40 to 50, 35 to 50 or 40 to 55° C., e.g. about 35, 40, 45, 50 or 55° C. Additionally or alternatively the particles may be compressed in order to cause them to form a solid mass of particles. As a further alternative an adhesive substance, e.g. a glue or polymer, may be used to adhere the particles. The glue or polymer may be degradable under conditions of degradation of the first polymer, so that, in use, the particles separate in order to facilitate release of the releasable material. In a further option the microparticles may be embedded in a substance, e.g. a gel, a wax etc. This may be degradable, meltable or otherwise removable under conditions of use, e.g. under conditions under which the first polymer degrades.

The microparticles (and hence the substance comprising said microparticles) of the invention may be made by combining a first solution comprising the first polymer in a first solvent, and a second solution comprising a second polymer in a second solvent, to form a mixed polymer solution. Alternatively, the first and second polymers may be dissolved in a solvent, optionally a mixed solvent comprising the first and the second solvent. The first and second solvents may be the same or may be miscible and different. The mixed polymer solution is then emulsified in a medium in which the first and second solvents are at most sparingly miscible (commonly an aqueous medium) to form an emulsion. The emulsion is then aged for sufficient time to allow for at least partial separation of the first polymer and the second polymer within droplets of the emulsion so as to form a core comprising the first polymer and a shell surrounding the core and comprising the first polymer and the second polymer. The first and second solvents are then depleted from the droplets of the emulsion so as to form the microparticles as an aqueous suspension.

In a preferred option the first and second solvents are the same. The first solvent should be a solvent for the first polymer and the second solvent should be a solvent for the second polymer. Commonly the first and second solvents are hydrophobic solvents. They may, independently, be aromatic hydrocarbon solvents, halogenated solvents, ester solvents, ketone solvents or some other suitable solvents, or may be a mixture of suitable solvents. A suitable solvent for both first and second solvents is dichloromethane (DCM). Other suitable solvents include or other suitable solvent such as DMF, DMSO, methanol or a mixture of any one or more of these with DCM. In one example, a minimal quantity of DMF and/or DMSO and/or methanol is used to aid in dissolving some types of drugs before mixing the solubilised drug with a PLGA-DCM solution so as to improve the incorporation of drug into the PLGA-DCM solution. If the solid drug is instead added directly to the PLGA-DCM, it may in some cases precipitate out into the PLLA phase or into the emulsifying buffer solution during synthesis. The continuous phase of the emulsion is commonly aqueous. It may comprise water together with one or more solutes. These may be polymeric, for example methyl cellulose. The solute may be present at a level of about 0.01 to 1% by weight, or about 0.01 to 0.1, 0.1 to 1 or 0.05 to 0.5%, e.g. about 0.01, 0.05, 0.1, 0.5 or 1%. The emulsion may be stabilised by means of a surfactant. The surfactant may be non-toxic. It may be biodegradable. In order to prevent premature depletion of the first and second solvents from the droplets of the emulsion, the continuous phase may have small amounts of the first and/or second solvents dissolved therein. It may be saturated with the first and/or second solvents. It may additionally or alternatively comprise the releasable material. It may be saturated with the releasable material.

The concentration of the first polymer in the first solvent and, independently, of the second polymer in the second solvent, may be about 5 to about 50% w/v, or about 5 to 20, 5 to 10, 10 to 50, 20 to 50 or 10 to 20%, e.g. about 5, 10, 15, 20, 25, 30, 35, 40, 45 or 50%.

The medium in which the mixed polymer solution is emulsified may be aqueous. It may be an aqueous solution. It may comprise an emulsifying agent. The emulsifying agent may be a polymeric emulsifying agent. It may be a surfactant. It may be a monomeric surfactant or may be a polymeric surfactant. It may be non-ionic or may be cationic or may be anionic or may be zwitterionic. The aqueous solution may also comprise a cosurfactant. Suitable emulsifying agents include methylcellulose, polysorbate/sorbitan surfactants e.g. Tween®, Span®, polyoxyethylene surfactants eg. Brij®, ethylenoxide and propylenoxide surfactants eg. Pluronic®, etc.

As discussed elsewhere, the release of the releasable material, if present, may be controlled by factors including the molecular weight of the first polymer, the chemical nature (and hence rate of degradation) of the first polymer, the particle size of the releasable substance or of support particles on which it is adsorbed and/or absorbed and in some instances the ratio of first polymer to second polymer. The process may therefore comprise the step of selecting one or more of: the molecular weight of the first polymer, the chemical nature (and hence rate of degradation) of the first polymer, the particle size of the releasable substance or of support particles on which it is adsorbed and/or absorbed and the ratio of first polymer to second polymer, in order to achieve a desired release characteristic of the releasable material in the intended application. The release characteristic may be a release delay or lag time (i.e. time following exposure of the particles to conditions under which the first polymer degrades until release commences) or may be a rate of release once release commences. The delay or lag time may be from about 0.5 to about 100 days, or from about 0.5 to 50, 0.5 to 20, 0.5 to 10, 0.5 to 5, 0.5 to 2, 0.5 to 1, 1 to 50, 50 to 50, 10 to 50, 20 to 50, 1 to 10, 5 to 20 or 10 to 20 days, e.g. about 0.5, 1, 1.5, 2, 2.5, 3, 3.5, 4, 4.5, 5, 6, 7, 8, 9, 10, 11, 12, 13, 14, 15, 20, 15, 30, 35, 40, 45 or 50 days, or may be more or less than this in particular cases. In some cases there may be no, or negligible, delay or lag time. The rate of release may be such that the releasable material is released over a period of from about 0.5 to about 100 days, or from about 0.5 to 50, 0.5 to 20, 0.5 to 10, 0.5 to 5, 0.5 to 2, 0.5 to 1, 1 to 50, 50 to 50, 10 to 50, 20 to 50, 1 to 10, 5 to 20 or 10 to 20 days, e.g. about 0.5, 1, 1.5, 2, 2.5, 3, 3.5, 4, 4.5, 5, 6, 7, 8, 9, 10, 11, 12, 13, 14, 15, 20, 15, 30, 35, 40, 45 or 50 days, or more or less than this in particular cases.

The first solution may also comprise the releasable material and may therefore be made by adding the releasable material to a solution of the first polymer in the first solvent or by dissolving the first polymer in a mixture of the first solvent and the releasable material (optionally on a support). The releasable material may be provided in particulate form or adsorbed onto a particulate support. The particles (either of the releasable material or of the support with the releasable material thereon and/or therein) may have a diameter of about 1 to about 20 nm, or about 1 to 10, 1 to 5, 1 to 2, 2 to 20, 5 to 20, 10 to 20, 2 to 10 or 5 to 10 nm, e.g. about 1, 2, 3, 4, 5, 6, 7, 8, 9, 10, 11, 12, 13, 14, 15, 16, 17, 18, 19 or 20 nm, or may be larger (e.g. about 30, 40, 50 or 100 nm) or smaller than this. In the discussion below, it is assumed that a releasable material is present. However it should be recognised that in some cases there is no releasable material other than the first polymer. In this case the process is the same, with omission of the releasable substance and, if present, a support on which it is adsorbed/absorbed.

By combining the first and second solutions, a solution is formed in which the first and second polymers are present, as well as the releasable substance, commonly although not always in suspension or adsorbed onto particles. This mixed polymer solution is then emulsified in a medium so that the mixed polymer solution forms the dispersed phase (droplets) of the emulsion. The droplets may be between about 1 to about 1000 microns in diameter, or about 1 to 500, 1 to 200, 1 to 100, 1 to 50, 1 to 20, 1 to 10, 10 to 1000, 100 to 1000, 500 to 1000, 10 to 100, 10 to 50 or 50 to 100 microns, e.g. about 1, 2, 3, 4, 5, 6, 7, 8, 9, 10, 15, 20, 25, 30, 35, 40, 45, 50, 60, 70, 80, 90, 100, 150, 200, 250, 300, 350, 400, 450, 500, 600, 700, 800, 900 or 1000 microns. The process may comprise agitating (e.g. shaking, sonicating, micronising etc.) a mixture of the medium and the mixed polymer solution so as to achieve a desired droplet size.

Once the emulsion is formed, sufficient time should be allowed for phase separation to occur so as to form a structure in which a core solution which is rich in the first polymer relative to the second polymer is surrounded by a shell solution which is rich in the second polymer relative to the first polymer. The shell solution should however contain some of the first polymer (commonly less than about 25% relative to the second polymer).

In order to solidify the polymers in order to form the particles, the first and/or second solvents should be depleted from the particles. A convenient means to achieve this is to dilute the emulsion with a mixture miscible with the continuous phase (commonly an aqueous liquid) having none of the first and/or second solvent therein. The solvent then partitions out of the droplets so as to allow the first and second polymers to solidify. The dilution may be conducted rapidly or gradually. Thus the emulsion may be added, optionally with stirring, to the diluting continuous phase or else the diluting continuous phase may be added to the emulsion, commonly gradually added with stirring. Other means to achieve depletion of the solvent(s) in the droplets may readily be appreciated, for example by heating the emulsion to a temperature near, at or above the boiling point of the first and/or second solvent, or applying a partial vacuum to the emulsion so as to evaporate the first and/or second solvent. For these methods it is preferable that the first and/or second solvents be lower boiling than the continuous phase of the emulsion.

It is thought that as the first and/or second solvents are withdrawn from the particles of the droplets, the core solution forms the core of the particles in which (if the releasable material is in particulate form or adsorbed onto a particulate support) the releasable material or support particles are dispersed. The shell solution surrounding the core forms a shell. As the solvent is removed from the shell solution further phase separation occurs within the shell, forming channels of the first polymer through a shell matrix of the second polymer. It should be understood, however that there may be a minor amount of mutual miscibility of the first and second polymers, whereby the first polymer in the core may comprise a small amount of the second polymer, and the second polymer of the shell may similarly comprise a small amount of the first polymer.

Once the particles have been fully formed, they may be separated from the resulting suspension by any commonly used method, e.g. filtration, centrifugation, settling/flotation, evaporation etc. They may then be washed to remove residues of unwanted materials such as solutes in the continuous phase, surfactants etc. and may then be dried.

The present invention allows for the tailoring of different release profiles by mixing batches of particles with different characteristics to form a composite substance. For example if two separate releasable materials are to be released simultaneously, they may be separately incorporated into the cores of otherwise identical microparticles. These may then be combined into a single composite substance which would release the two releasable materials simultaneously. Alternatively, if the two releasable materials are to be released sequentially, the shells of a first batch of microparticles comprising a first releasabable material (in the cores thereof) may be designed for a short or negligible delay and a second batch comprising a second releasable material in the cores may be designed such that the shells have a delay corresponding to the delay of the first batch plus the release time of the second batch. In this way the resulting composite substance would release the two releasable substances sequentially. In a further option, a single releasable substance may be incorporated into two batches of microparticles designed so that the delay of the second batch is greater than the delay of the first batch plus the release time of the first batch. In this way, the releasable substance would be delivered in two discrete phases with a gap between them when no release would occur. Skilled workers will readily recognise that other release profiles may be prepared at will by combination of two or more dissimilar batches of microparticles according to the invention. This versatility is provided by the ability to independently control the rate of release of the releasable substance and the delay time before release occurs, as discussed earlier.

In some applications the microparticles of the invention may be administered to a patient. This may for the purposes of treatment of a condition for which the releasable material is indicated, or may be for imaging of a portion of the body wherein the releasable material is an imaging agent (e.g. an MRI imaging agent, a PET imaging agent etc.). The administration may be by ingestion, inhalation, suppository, injection or by some other suitable route. The microparticles, or the substance comprising the microparticles may be used for the manufacture of a medicament for treatment of a conditions. Treatable diseases in this context may include pain, fever, cancer, microbial infections etc. The technology may be suitable for release of hydrophobic (e.g. water insoluble) substances, e.g. hydrophobic drugs, although hydrophilic (e.g. water soluble) drugs or other releasable substances may also be used.

This technology may be used to deliver drugs, proteins and/or other active ingredients for various applications including orthopedics, vision care, consumer products, and food/nutritional products. It provides the following unique features:

Tunable lag time before the release of drugs, proteins and/or active ingredients.

Possibility of combining multiple delayed release formulations for the controlled release of different drugs, proteins and/or active ingredients in a predetermined sequence.

Possibility of combining multiple delayed release formulations to release the same drug, protein or active ingredient repeatedly in a pulsatile manner, or for long-term sustained release.

Possibility for large-scale generation of microspheres for in vivo applications or commercial products.

Possibility of delivering and retaining microspheres easily in a desired implantation site by either (i) compaction at a raised temperature, or (ii) encapsulation in a carrier such as hydrogel, membrane and scaffold.

EXAMPLES

Figure 2:
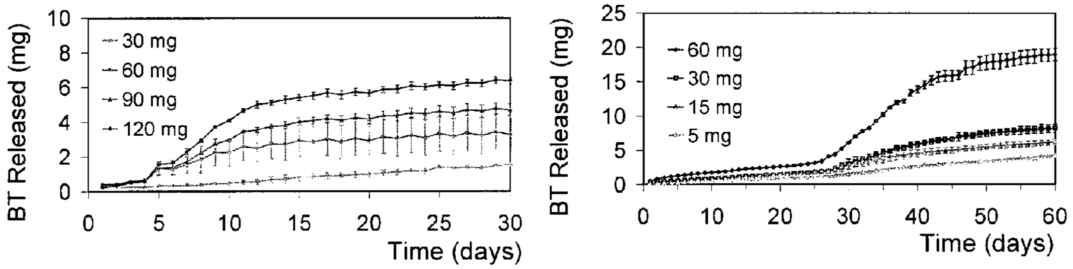
FIG. 2 shows graphs of brimonidine tartarate (BT) drug release profile using core-shell PLLA-PLGA microspheres with a PLLA:PLGA weight ratio of 1:1, PLLA of 100 kDa, and PLGA of 7 kDa (left) and 24 kDa (right). The amounts of BT loaded in 250 mg of microspheres are specified in the key. 7 kDa PLGA resulted in a 4-day lag time, while 24 kDa PLGA resulted in a 25-day lag time before drug release.
Figure 3:
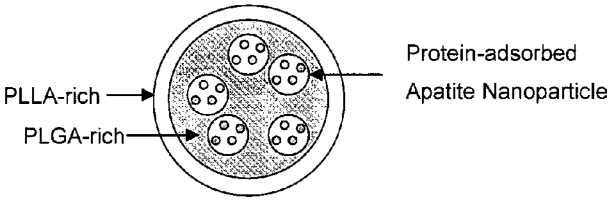
FIG. 3 is a diagram illustrating additional inorganic apatite nanoparticles loaded in the PLGA-rich core phase allowed for the adsorption and delivery of proteins.
Figure 4:
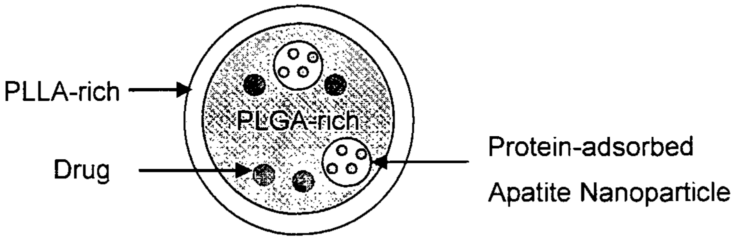
FIG. 4 is a diagram illustrating combined delivery of both drugs and proteins.
Figure 5:
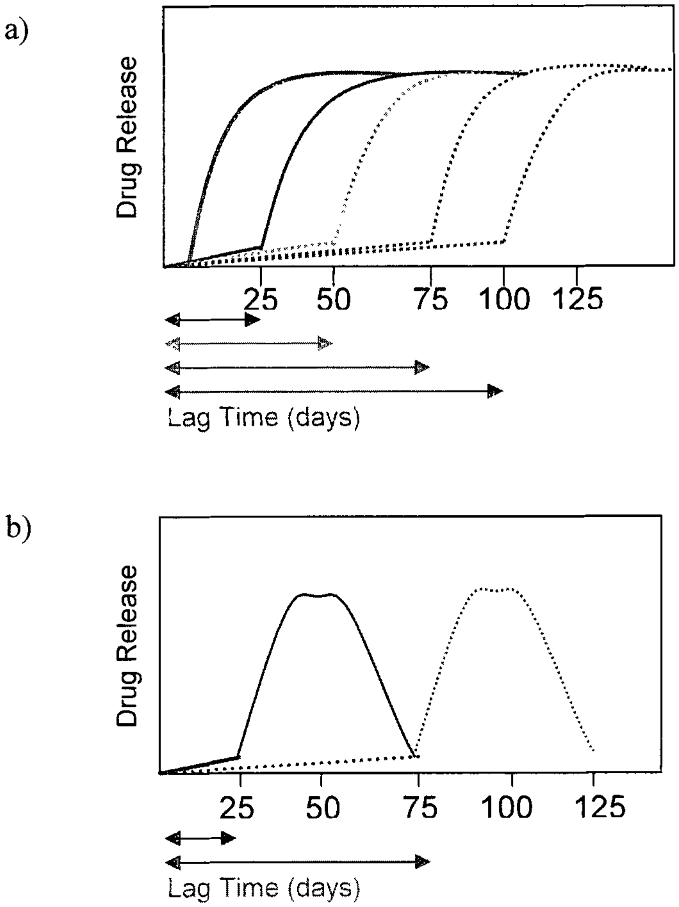
FIG. 5 shows graphs of (a) long-term and (b) pulsatile release of drugs and/or proteins by combining core-shell microspheres with different lag times.
Figure 6:
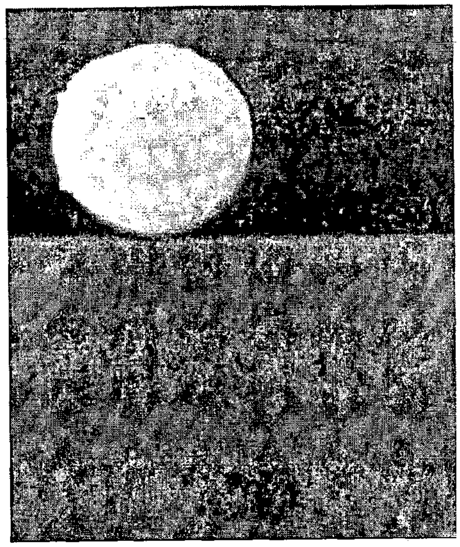
FIG. 6 is a photograph of a pellet of microspheres achieved by compaction.
Figure 7:
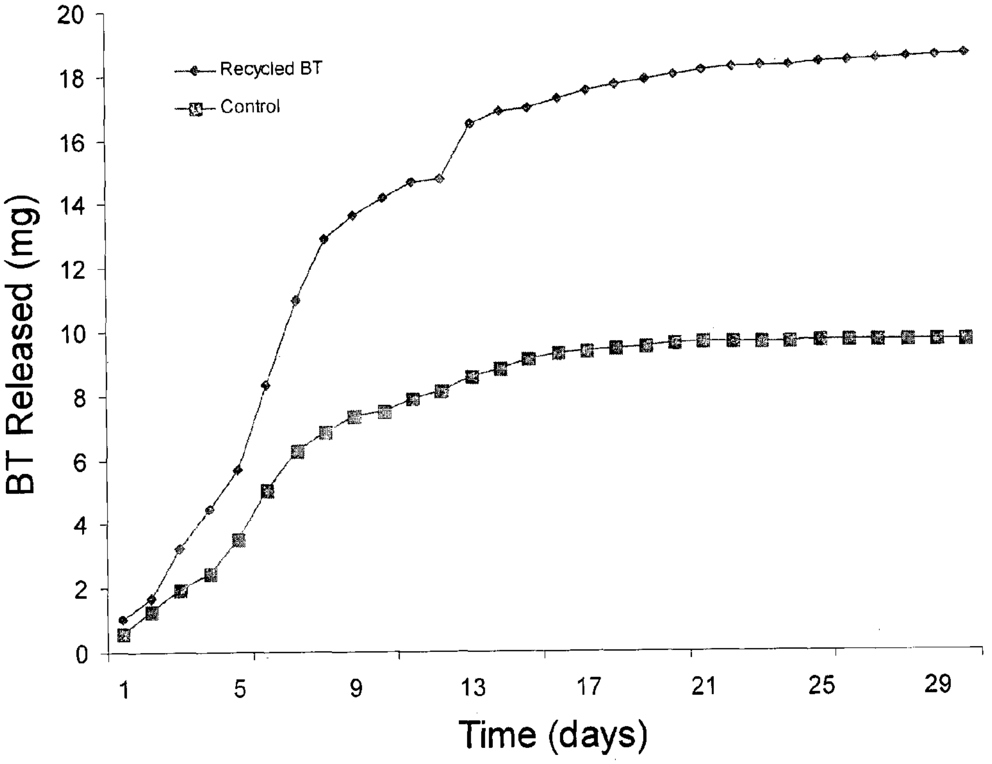
FIG. 7 is a graph illustrating that introducing a saturated drug solution in the aqueous phase allowed for improved drug loading onto the microspheres.
Figure 9:
FIG. 9 shows photographs of how compacts of microspheres were inserted in the space by the (a) left and (b) right knee joints.
Figure 14:
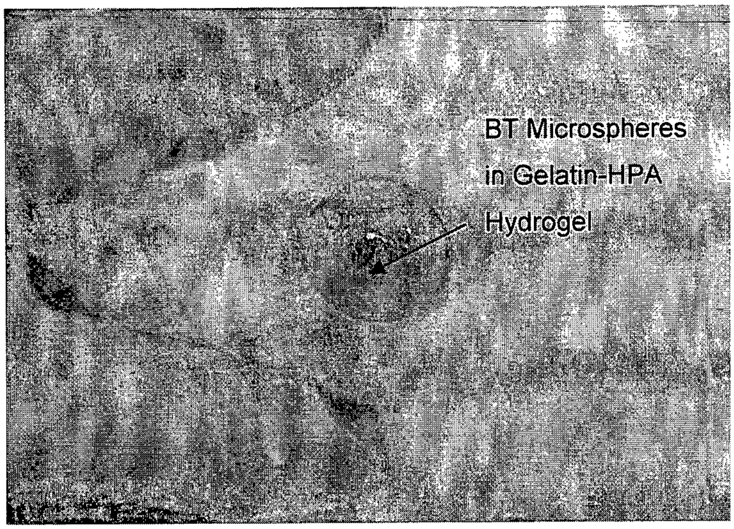
FIG. 14 is a photograph showing encapsulated microspheres in the eye of a rabbit. Core-shell PLLA-PLGA microspheres were synthesized using a PLLA:PLGA weight ratio of 1:1, PLLA of 100 kDa, and PLGA of 24 kDa. They were loaded with BT and encapsulated in a gelatin-HPA hydrogel carrier, which was inserted into the eye of a rabbit induced with glaucoma.

Core-shell nanocomposite microspheres with poly(D,L-lactic-co-glycolic acid) (PLGA)-rich core and poly(L-lactic acid) (PLLA)-rich shell were developed as delayed release vehicles for the sequential delivery of single or multiple drugs. The core-shell structure was formed by controlled phase separation of PLLA and PLGA. Drugs were incorporated into the PLGA phase (core). PLGA degradation would create pores in the PLLA-rich shell so that the drugs could be released by diffusion through the PLLA-rich shell (FIG. 1). The lag time before drug release was therefore controlled by the PLGA degradation time, which was dependent on its molecular weight (FIG. 2). Additional inorganic (apatite) nanoparticles incorporated in the PLGA phase would facilitate the adsorption and delivery of proteins (FIG. 3). Proteins might be released from the microspheres through the degradation of the PLGA-rich core, which led to acid production and dissolution of apatite nanoparticles, and the subsequent release of proteins that were pre-adsorbed onto the apatite nanoparticles. By incorporating drug- and protein-adsorbed inorganic nanoparticles into the PLGA phase, both drugs and proteins could be concurrently released while minimizing total microsphere volume (FIG. 4). Long-term sustained release of drugs and/or proteins could be achieved by combining microspheres of different PLGA molecular weights (FIG. 5*a*). Pulsatile release would also be possible (FIG. 5*b*). The microspheres could be compacted as pellets for ease of implantation (FIG. 9). Alternatively, they could be incorporated into a carrier such as a hydrogel, membrane or scaffold, and replaced when the drugs and/or proteins have been completely released (FIG. 14).

A1. Preparation of Core-Shell Microspheres

A1.1. PLLA-PLGA Microspheres for Drug Delivery

PLLA-PLGA core-shell microspheres were synthesized using a solid-in-oil-in-water emulsion solvent extraction technique. In a typical synthesis, two separate solutions of 125 mg of PLLA in 1 ml of dichloromethane (DCM) and 125 mg of PLGA in 1 ml of DCM were prepared. Up to 125 mg of drug was then added to the PLGA solution to form a solid-in-oil suspension. This suspension and the PLLA solution were combined, mixed, and subsequently emulsified in 200 ml of 0.1 wt % methyl cellulose solution in water using a mechanical stirrer with a stirring speed of 400 rpm to produce a solid-in-oil-in-water emulsion. The methyl cellulose solution used in this emulsification step was partially saturated with 1.8 ml of DCM to minimize unwanted extraction of DCM from the oil droplets by water, and prevent prematured hardening of microspheres before the two polymers could phase separate. Controlled extraction of DCM and hardening of polymer droplets were later initiated after 30 min of stirring by adding another 200 ml of 0.1 wt % methyl cellulose solution that contained no DCM using a peristaltic pump at a rate of 1-7 ml/min. Stirring continued for another 4 h to ensure complete DCM extraction. The hardened microspheres obtained were filtered, washed with water, and freeze-dried overnight.

A1.2. PLLA-PLGA-Apatite Microspheres for Protein Delivery

Etidronate-capped carbonated apatite (eCAP) nanoparticles were synthesized by the base precipitation of calcium nitrate with ammonium hydrogen phosphate in the presence of diphosphonic acid molecules (e.g. etidronic acid: 1-hydroxyethane 1,1-diphosphonic acid) to reduce the particle agglomeration. In a typical synthesis, 100 ml of calcium nitrate solution (8 mM) was quickly added to 100 ml of a base solution consisting of ammonium hydrogen phosphate (5 mM), ammonium hydrogen carbonate (5 mM), etidronic acid (3 mM), and ammonium hydroxide (pH 10.4) to yield eCAP nanoparticles. After 24 h, the nanoparticles were concentrated and washed with water by ultrafiltration to remove any unreacted reagents. 8.5 mg of protein was then added to 20 mg of eCAP particles, and the suspension was stirred overnight to allow the adsorption of protein onto the eCAP nanoparticles. The resulting suspension were concentrated and washed with water by ultrafiltration to remove any unbound proteins. The particles were then freeze-dried overnight to yield protein-loaded eCAP.

Two separate solutions of 125 mg of PLLA in 1 ml of DCM and 125 mg of PLGA in 1 ml of DCM were then prepared. 30 mg of protein-loaded eCAP was then added to the PLGA solution to form a solid-in-oil suspension. This suspension and the PLLA solution were combined, mixed, and subsequently emulsified in 200 ml of 0.1 wt % methyl cellulose solution in water using a mechanical stirrer with a stirring speed of 400 rpm to produce a solid-in-oil-in-water emulsion. The methyl cellulose solution used in this emulsification step was partially saturated with 1.8 ml of DCM to minimize unwanted extraction of DCM from the oil droplets by water and prevent prematured hardening of microspheres before the two polymers could phase separate. Controlled extraction of DCM and hardening of polymer droplets were later initiated after 30 min of stirring by adding another 200 ml of 0.1 wt % methyl cellulose solution that contained no DCM with a peristaltic pump at a rate of 1-7 ml/min. Stirring continued for another 4 h to ensure complete DCM extraction. The hardened microspheres obtained were filtered, washed with water, and freeze-dried overnight.

A1.3. Microspheres for Combined Drug and Protein Delivery

The protein-adsorbed eCAP nanoparticles were prepared as described in Section A1.2 above. Both the protein-adsorbed eCAP nanoparticles and drugs could be loaded in combination into the PLGA solution to form a solid-in-oil suspension. This suspension and the PLLA solution were then combined, and subjected to the various steps as described in Section A1.2 above.

A2. Large-Scale Production of Microspheres

The protein-loaded PLLA/PLGA core-shell microspheres were synthesized using a solid-in-oil-in-water emulsion solvent extraction technique. In a typical synthesis, two separate solutions of 12.5 g of PLLA in 100 ml of DCM and 12.5 g of PLGA in 100 ml of DCM were prepared. Up to 10 g of dyes, drugs or proteins were then added to the PLGA solution to form a solid-in-oil suspension. This suspension and the PLLA solution were combined, mixed, and subsequently emulsified in 600 ml of 0.1 wt % methyl cellulose solution in water using a mechanical stirrer with a stirring speed of 400 rpm to produce a solid-in-oil-in-water emulsion. The methyl cellulose solution used in this emulsification step was partially saturated with 5.4 ml of DCM to minimize unwanted extraction of DCM from the oil droplets by water, and prevent prematured hardening of microspheres before the two polymers could phase separate. Controlled extraction of DCM and hardening of polymer droplets were later initiated after 30 min of stirring by adding another 600 ml of 0.1 wt % methyl cellulose solution that contained no DCM with a peristaltic pump at a rate of 1-7 ml/min The mixture was further stirred for 24 h to ensure complete extraction of DCM. The hardened microspheres obtained were filtered, washed with water, and freeze-dried overnight.

A2.1. Procedures for Scale Up by 100×

1. Dissolve 12.5 g of PLLA (90 kDa) in 100 ml of DCM in a glass vial, which was covered to prevent evaporation.

2. Dissolve 12.5 g of PLGA (e.g. 7 kDa, 24 kDa) in 100 ml of DCM in a glass vial, which was covered to prevent evaporation.

3. Add up to 10 g of drug or protein to the PLGA solution, and mix it to form a solid-in-oil suspension.

4. Add the PLGA-drug mixture to the PLLA solution, and mix.

5. Mix the above solution with 600 ml of methyl cellulose surfactant solution (0.1 wt %, 1 g/L of phosphate buffered saline (PBS)) saturated with 5.4 ml of DCM using a mechanical stirrer with a stirring speed of 400 rpm for 30 min to produce a solid-in-oil-in-water emulsion.

6. While continuing to stir, add another 600 ml of methyl cellulose surfactant solution (0.1 wt %, 1 g/L in PBS) without DCM, using a peristaltic pump.

7. Centrifuge at 1500 rpm for 4-5 min, and pour off the methylcellulose.

8. Wash and spin down several times with water until the water is clear and no longer violet. Air dry the microspheres obtained.

A2.2. Procedures for Scale Up to Kilograms

1. Dissolve 1.25 kg of PLLA (90 kDa) in 10 l of DCM in a vessel.

2. Dissolve 1.25 kg of PLGA (e.g. 7 kDa, 24 kDa) in 10 l of DCM in a vessel.

3. Add up to 1 kg of drugs or proteins to the PLGA solution, and mix to form a solid-in-oil suspension.

4. Add the PLGA-drug mixture to the PLLA solution, and mix.

5. Mix the above solution with 60 l of methyl cellulose surfactant solution (0.1 wt %, 1 g/L of PBS) saturated with 540 ml of DCM using a mechanical stirrer with a stirring speed of 400 rpm for 30 min to produce a solid-in-oil-in-water emulsion.

6. While continuing to stir, add another 60 l of methyl cellulose surfactant solution (0.1 wt %, 1 g/L of PBS) without DCM using a peristaltic pump at 1 ml/min.

7. Centrifuge at 1500 rpm for 4-5 min and pour off the methyl cellulose.

8. Wash and spin down several times with water until the water is clear and no longer violet. Air dry the microspheres obtained.

A3. Methods for Delivering and Retaining Microspheres at the Desired Implantation Site A3.1. Compaction at a Raised Temperature By subjecting them to the glass transition temperature (lower limit: 45-50° C.) of the PLLA outer shell, the microspheres were not melted or damaged, and could be mechanically separated again. This would not work if the microspheres were loaded with proteins or drugs that could not be subjected to temperatures above 45° C.

The microspheres were compacted into pellet of cylindrical or other shapes by applying heat with/without centrifugation. Typically, the microspheres were either poured or centrifuged into the molds. The filled molds were then placed in an oven at 45-50° C. for 24 h. Holding the microspheres at the lower limit of the glass transition temperature of the PLLA outer shell enabled a slight softening of the PLLA, allowing the microspheres to stick to one another lightly. Upon removal from the molds, the microspheres remained in the desired shape of the molds, but could be separated again undamaged by applying a moderate force or friction.

A3.2. Procedure for Obtaining Highly Compacted Microspheres

1. In the final washing and spinning down step for microsphere synthesis, the microspheres should be spun down in batches of the desired pellet quantity. For example, if 100 g of dry raw materials were used to make pellets of 10 g each, split the samples equally into 10 individual tubes before centrifugation.

2. Pour off the solution on the top, leaving only the solids at the bottom of the centrifuge tubes.

3. Directly place the tubes in the oven at 45-50° C. for 24 h.

4. The resulting microspheres are highly compacted, which would require a lot of force to separate the individual microspheres.

A3.3. Procedure for Obtaining Less Compacted Microspheres

1. In the final washing and spinning down step for microsphere synthesis, the microspheres should be spun down in batches of the desired pellet quantity. For example, if 100 g of dry raw materials were used to make pellets of 10 g each, split the samples equally into 10 individual tubes before centrifugation.

2. Pour off the solution on the top, leaving only the solids at the bottom of the centrifuge tubes.

3. Add a small quantity of water, and vortex to loosen the microspheres.

4. Place the tubes in the oven at 45-50° C. for 24 h.

5. The resulting microspheres are less compacted than in Section A3.2 above, and are more easily separated.

A3.4. Procedure for Obtaining Highly Compacted Microsphere in a Mini-Tablet Form A hydraulic press was employed to compact the microspheres and minimize the volume of the microsphere pellet. This facilitated the insertion of the microspheres into specific implantation sites, especially those (e.g. the eyes) that have space constraints.

1. After freeze-drying, the microspheres are weighed to provide the desired amount of drugs to be delivered.

2. Transfer the microspheres onto a tablet die punch of the desired dimensions.

3. Place the tablet die punch containing the microspheres onto a hydraulic press.

4. Apply a suitable pressure with the hydraulic press to achieve a highly compacted tablet.

5. Remove the tablet from die punch.

A4. Methods for Increasing the Drug Loading Capacity of Microspheres

By increasing the amount of drugs loaded into the PLGA core, a longer sustained release could be achieved with the microspheres.

A4.1. Procedure for Increasing Loading by Reusing Drug-Saturated Emulsifying Solution Reusing the drug-saturated emulsifying solution obtained from previous microspheres fabrication steps allowed for the establishment of equilibrium in the drug amount between the internal and external environments of the emulsifying droplets, reducing the net loss of drugs to the surrounding aqueous solution.

1. Using mechanical vortexing, dissolve 125 mg of PLLA (100 kDa) in 1 ml of DCM in a glass vial, which is covered to prevent evaporation.

2. Using mechanical vortexing, dissolve 125 mg of PLGA (7 kDa, 12.9 kDa, 24 kDa or other molecular weights) in 1 ml of DCM in a glass vial, which is covered to prevent evaporation.

3. Add up to 120 mg of drugs to the PLGA solution, and mix to form a solid-in-oil suspension.

4. Add the PLGA-drug mixture to the PLLA solution, and mix to produce a drug-PLGA-PLLA suspension.

5. To a beaker, add 200 ml of reused methyl cellulose surfactant solution (0.1 wt %, 1 g/L of PBS) containing the same drug used to load the microspheres. Partially saturate the solution with 1.8 ml of DCM.

6. Using an overhead stirrer with a stirring speed of 250 rpm, add the drug-PLGA-PLLA suspension from step 4 to the surfactant solution in step 5 to produce a solid-in-oil-in-water emulsion.

7. After 30 min, while continuing to stir at 250 rpm, use a peristaltic pump to add another 200 ml of reused methyl cellulose surfactant solution (0.1 wt %, 1 g/L in PBS) containing the same drug used to load the microspheres. This also controls the DCM solvent extraction rate.

8. Stir for 6 h to overnight so that the DCM is completely extracted.

9. Centrifuge at 2500-3000 rpm for 5 min, and decant off the surfactant solution. Keep the hard microspheres collected at the bottom. This step is to separate the properly formed microspheres from the excess polymer.

10. Wash the microspheres 3 times with PBS and spin down in between each wash. This step removes the excess unencapsulated drugs on the microspheres.

A5. Encapsulation of Microspheres in a Carrier (e.g. Hydrogel, Membrane and Scaffold)

The microspheres were suspended in the liquid state in hydrogels, such as gelatin-hydroxyphenylpropionic acid (HPA), gelatin-oligomeric (−)-epigallocatechin-3-O-gallate (OEGCG), hyaluronic acid (HA)-tyramine, and HA-OEGCG. They were then injected into the desired implantation site, following which the hydrogel would solidify via a crosslinking reaction (e.g. enzyme-mediated reaction catalysed by horseradish peroxidase (HRP) and hydrogen peroxide for HA-tyramine).

Prepare freeze-dried or air-dried drug- or protein-encapsulated microspheres.

1. Prepare hydrogel solutions such as gelatin-HPA, gelatin-OEGCG, HA-tyramine, HA-OEGCG.

2. Vortex microspheres and hydrogel solution homogeneously.

3. Right before injection into the desired implantation site, mix in the reagents for crosslinking the hydrogel (e.g. HRP and hydrogen peroxide solutions for the HA-tyramine system).

4. Inject the mixed solution into the desired site using a needle of ≤18 g. Alternatively, inject the solution into a mold of the desired dimensions, and allow it to set into a fixed shape (e.g. disc) before implantation. Microspheres may also be entrapped in a porous polymeric material or scaffold by mixing the microspheres suspension with the polymer or scaffold solution prior to the curing of the latter.

Drug Delivery Using Core-Shell Polymer Microspheres

B1. Delivery of Bupivacaine to the Goat Knee Joint for >2 Weeks for Post-Surgical Pain Relief This test was performed by a third party GLP-certified company (Aginko AG) as part of a proof-of-concept study to determine the feasibility of delivering bupivacaine analgesia at therapeutic levels to the knee joint to relieve post-operative pain for at least 2 weeks following knee surgery.

Figure 8:
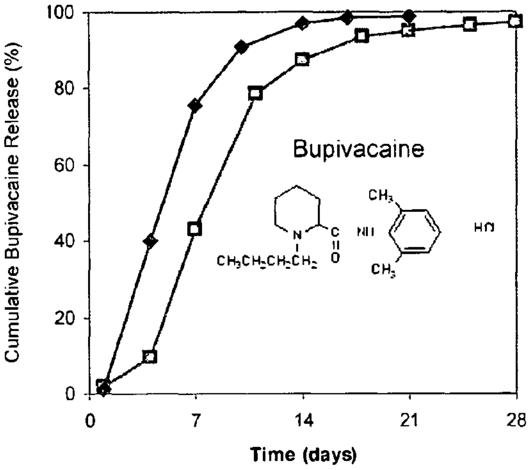
FIG. 8 is a graph illustrating in vitro release of bupivacaine by core-shell PLLA-PLGA microspheres synthesized with a PLLA:PLGA weight ratio of 1:1, with PLLA of 100 kDa, and PLGA of (♦) 7 kDa and (■) 24 kDa.

In this study, bupivacaine was loaded in core-shell PLLA-PLGA microspheres synthesized using a PLLA:PLGA weight ratio of 1:1, with PLLA of 100 kDa and PLGA of 24 kDa. This was based on preliminary in vitro release studies that showed that this combination of PLLA and PLGA enabled bupivacaine (30 wt % loading) to be released over >14 days (FIG. 8).

For the purpose of the in vivo study, the microspheres synthesis protocol was scaled up 100× as follows. The protein-loaded PLLA-PLGA core-shell microspheres were synthesized using a solid-in-oil-in-water emulsion solvent extraction technique. In a typical synthesis, two separate solutions of 12.5 g of PLLA in 100 ml of DCM and 12.5 g of PLGA in 100 ml of DCM were prepared. Up to 10 g of bupivacaine was then added in the PLGA solution to form a solid-in-oil suspension. This suspension and the PLLA solution were combined, mixed, and subsequently emulsified in 600 ml of 0.1 wt % methyl cellulose solution in water using a mechanical stirrer with a stirring speed of 400 rpm to produce a solid-in-oil-in-water emulsion. The methyl cellulose solution used in this emulsification step was partially saturated with 5.4 ml of DCM to minimize unwanted extraction of DCM from the oil droplets by water, and prevent prematured hardening of microspheres before the two polymers could phase separate. Controlled extraction of DCM and hardening of polymer droplets were later initiated after 30 min of stirring by adding another 600 ml of 0.1 wt % methyl cellulose solution that contained no DCM using a peristaltic pump at a rate of 1-7 ml/min. The mixture was further stirred for 24 h to ensure complete extraction of DCM. The hardened microspheres obtained were filtered, washed with water, and freeze-dried overnight.

For ease of handling during implantation, The microspheres were compacted into discs by pouring the microspheres into molds, and then placing the molds into an oven at 45-50° C. for 24 h. Holding the spheres at the lower limit of the glass transition temperature of the PLLA outer shell enabled slight softening of the PLLA to occur, allowing the microspheres to stick to each other lightly. Upon removal from the molds, the spheres remained in the desired shape of the mold, but could be separated again undamaged by applying a moderate force or friction. The microsphere compacts were easily implanted into the knee joints (FIG. 9).

Figure 10:
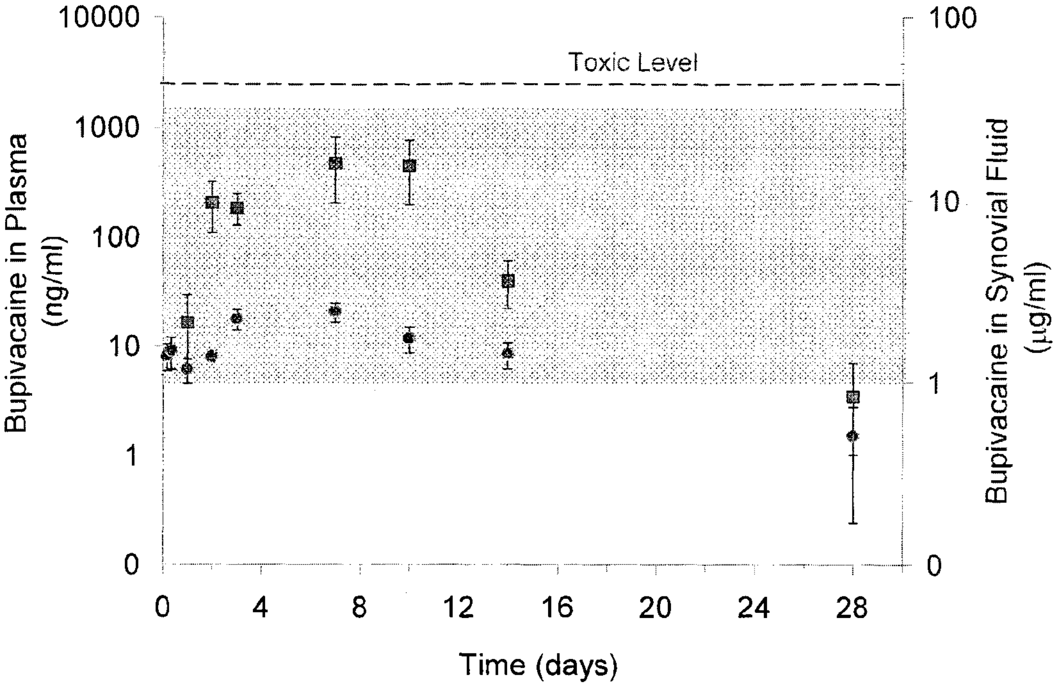
FIG. 10 shows Bupivacaine levels in (■) synovial fluid and (●) blood plasma as a function of time with the in vivo release of bupivacaine. The drug therapeutic window required for pain relief in the knee joint is indicated by the shaded area. The toxic limit of drug permissible in the blood plasma (4000 ng/ml) is indicated by the dotted line.
Figure 11:
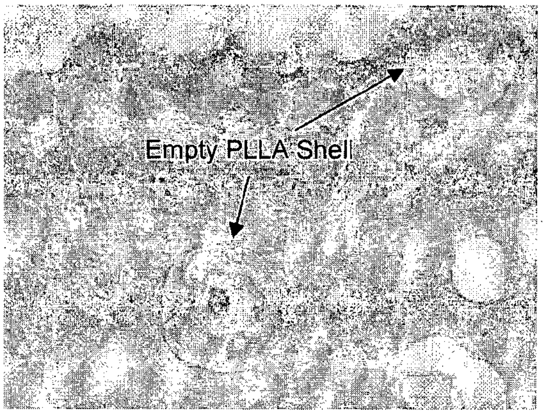
FIG. 11 shows a photograph of a histological section through the knee joint on day 28.

The in vivo studies showed that the therapeutic bupivacaine level was maintained in the knee joint for >2 weeks (FIG. 10). During this time, the bupivacaine level in the blood plasma was well below than the toxic limit, confirming safe, localized delivery of the drug. Histological sections through the knee joint at the end of the experiment showed no inflammation (FIG. 11). There was also no adverse reaction or loss of mobility reported.

Remnants of empty PLLA shells were observed in FIG. 11. However, since PLLA is an FDA-approved material commonly used in cosmetic fillers, no adverse effect was expected from its presence. We would be conducting further studies to monitor the animals until PLLA is completely degraded before proceeding to human trials. Use of a faster degrading PLLA so that the microspheres would completely degrade as soon as the drug has been fully released would not be feasible due to limitations on the relative PLLA and PLGA degradation rates (please see Section B3 below).

B2. Delivery of BT to Glaucoma Rabbit Eye to Reduce Intraocular Pressure (IOP)

BT is a drug used to reduce IOP in glaucoma patients. It is commonly administered in the form of eye drops 2-3 times a day. However, most of the drug is lost in tears, etc., during such administration. The goal of this study was to deliver BT more effectively and in a controlled, sustained manner via microspheres embedded in a carrier, which was implanted in the subconjunctiva of the eye. This carrier could be replaced 2-3 times per year.

Figure 12:
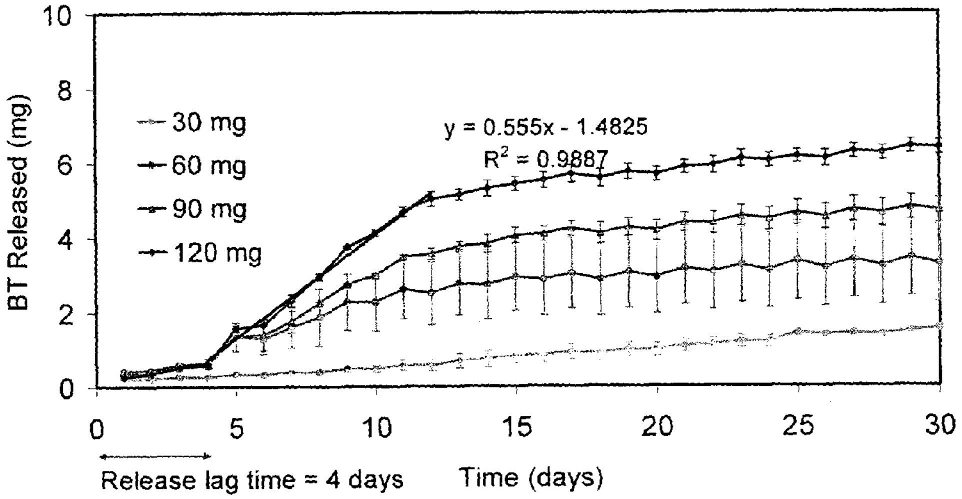
FIG. 12 shows a graph of BT release lag times and release rates obtained with core-shell PLLA-PLGA microspheres synthesized using a PLLA:PLGA weight ratio of 1:1, PLLA of 100 kDa, and PLGA of (a) 7 kDa and (b) 24 kDa. The amounts of BT loaded in 250 mg of microspheres are specified in the key. In (a), a lag time of 4 days was obtained, which was followed by a linear release of 0.56 mg/day over the next 8 days. In (b), a lag time of 25 days was obtained, which was followed by a linear release of 0.76 mg/day over the next 18 days.
Figure 12:
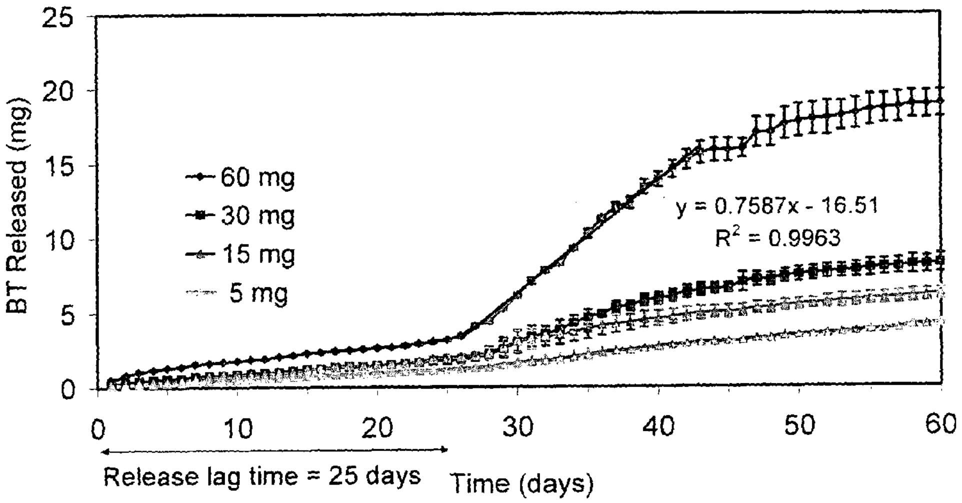
Figure 13:
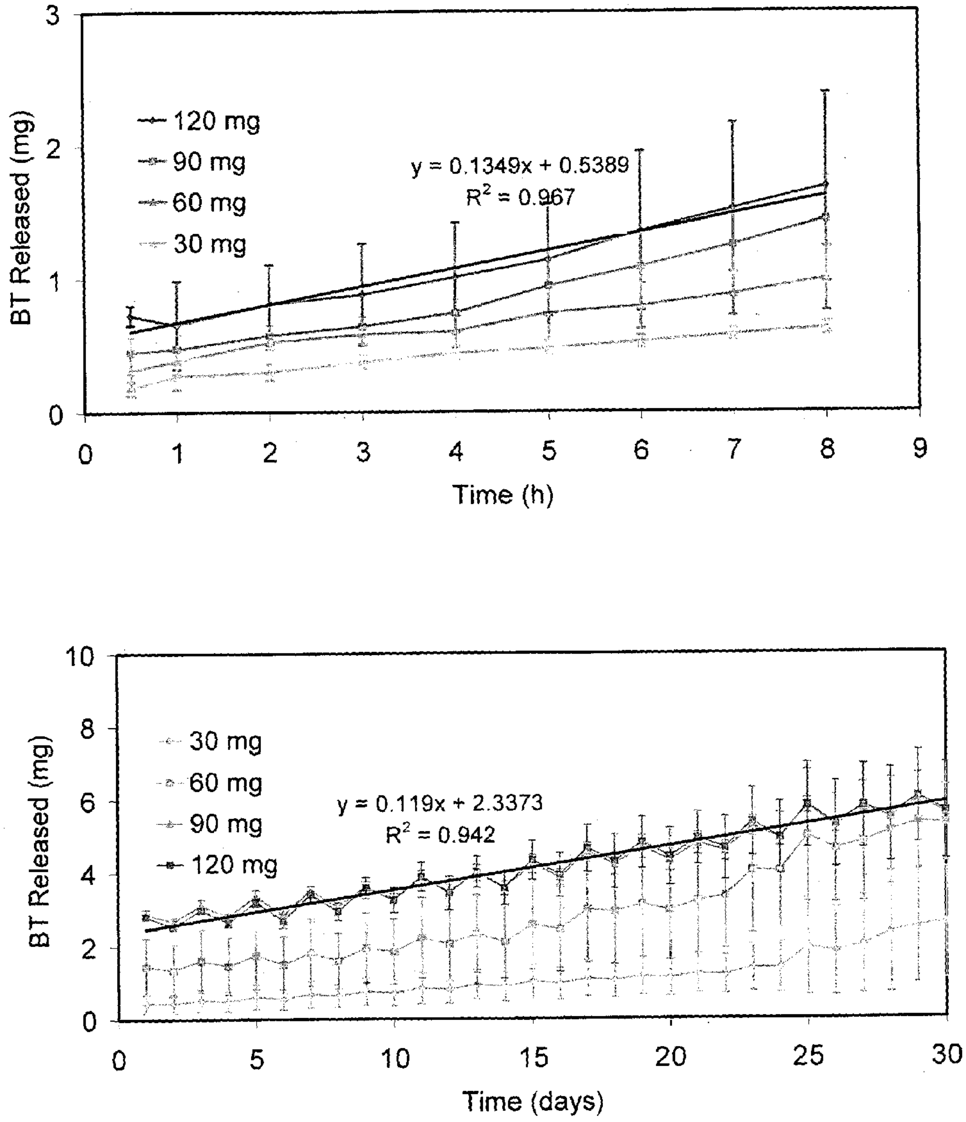
FIG. 13 shows BT release lag times and release rates obtained with core-shell PLLA-PLGA microspheres synthesized using a PLLA:PLGA weight ratio of 1:1, PLLA of 100 kDa, and PLGA of 3.4 kDa. The amounts of BT loaded in 250 mg of microspheres are specified in the key. No lag time was noticed when 3.4 kDa PLGA was used; and (a) a linear release rate of 0.13 mg/h was obtained in the first 8 h. Most of the BT was released in the first day, which was followed by (b) a reduced release rate of 0.12 mg/day. Based on the BT amount (2.8 mg) released after 1 day, it was calculated that the initial linear release occurred over the first 21 h.

In this study, BT was loaded in core-shell PLLA-PLGA microspheres synthesized using a PLLA:PLGA weight ratio of 1:1, PLLA of 100 kDa, and PLGA of 7 kDa and 24 kDa, so as to create microspheres of different release lag times (FIG. 12). When PLGA of the lowest available molecular weight (3.4 kDa, Lactel) was employed, BT release was found to occur immediately, with most of the drug released within the first day (FIG. 13).

Figure 15:
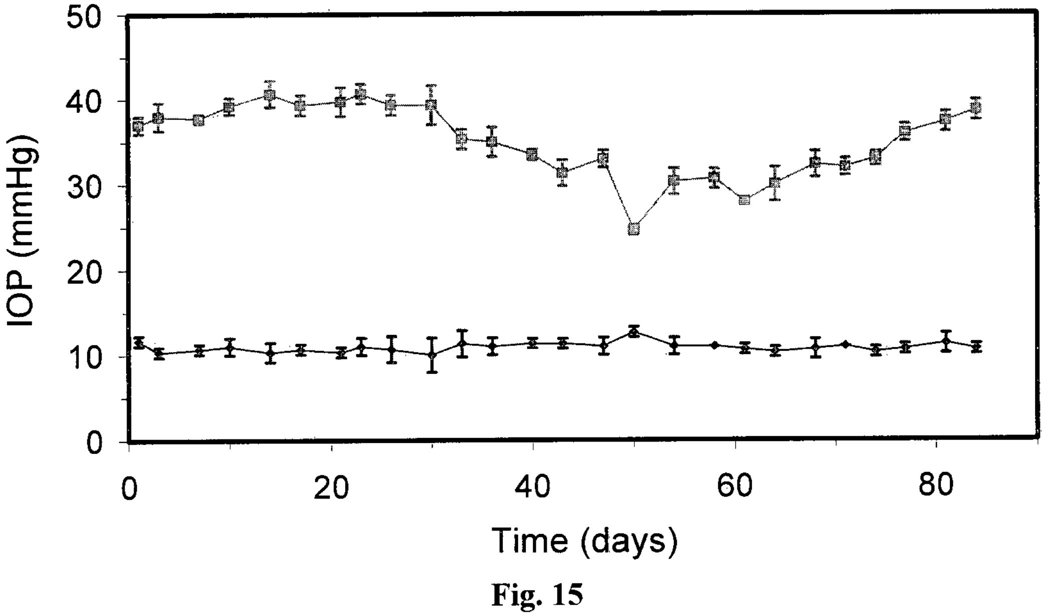
FIG. 15 is a graph illustrating that (■) IOP (intraocular pressure) levels decreased in the rabbits induced with glaucoma 30 days after implantation of the BT-loaded core-shell PLLA-PLGA microspheres, which were synthesized using a PLLA:PLGA weight ratio of 1:1, PLLA of 100 kDa, and PLGA of 24 kDa. They continued to decrease until day 50, and then slowly increased to the initial glaucoma IOP level on day 84. The microspheres were designed with an in vitro lag time of 25 days, followed by linear BT release for the next 18 days (see delivery profile in FIG. 12*b*). The IOP of normal rabbits is given as a reference (♦).

A batch of the core-shell PLLA-PLGA microspheres with PLGA of 24 kDa were loaded into a gelatin-HPA hydrogel carrier for ease of implantation into the subconjunctiva of the eye of rabbits induced with glaucoma (FIG. 14). The IOP decreased significantly from day 30 to day 50 post-implantation, and remained below the initial glaucoma levels until day 74 (FIG. 15). This indicated that there was no loss of function of the BT drug after encapsulation into the microspheres and in vivo implantation.

By combining core-shell PLLA-PLGA microspheres comprised of PLGA of different molecular weights, we could achieve sequential release of BT such that each new batch of microspheres would start releasing BT as soon as the previous batch of microspheres has finished releasing BT. This would enable long-term sustained release of BT. The combination of spheres could be compacted as described in Section A3 to reduce implant volume. The drug loading could also be increased as described in Section A4.

B3. PLLA and PLGA Molecular Weights and PLLA:PLGA Weight Ratios

PLLA should degrade much slower than PLGA in order to retain the shell barrier in the core-shell PLLA-PLGA microspheres during drug release. As the shell was PLLA-rich, once the PLGA degraded, pores would form in the shell so that the drug could be released via diffusion. The time required to degrade PLGA and PLLA was dependent on their molecular weights. Hence, a lower molecular weight PLGA could be combined with a lower molecular weight PLLA without affecting the release profile as long as PLLA would still degrade much slower than PLGA.

Although PLLA of 100 kDa was used in the present work, it is thought that PLLA of much higher molecular weights (>160 kDa) could be used, without affecting the sphere formation and release profile. PLGA of molecular weights higher than 75 kDa could be used to create longer lag times.

In general, changing the PLLA:PLGA weight ratios might result in core-shell inversion. For example, at a PLLA:PLGA weight ratio of 1:1 (the formulation used in the present experiments), microspheres with a PLGA-rich core and PLLA-rich shell were obtained. If a PLLA:PLGA weight ratio of 1:2 or 1:3 was used, phase inversion would occur yielding microspheres with a PLLA-rich core and a PLGA-rich shell. The optimal PLLA:PLGA weight ratios for deriving microspheres with a PLGA-rich core and a PLLA-rich shell would be 1:1 to 1:1.25.

Increasing PLLA relative to PLGA (e.g. PLLA:PLGA=2:1) would still yield microspheres with a PLGA-rich core and a PLLA-rich shell. However, it would change the core diameter and shell thickness ratio, resulting in a thicker shell relative to core. Thus, the range of workable PLLA:PLGA weight ratios is thought to be 2:1 to 1:1.25.

The present technology relates, in a particular embodiment, to a method for preparing microspheres, comprising poly(D,L-lactic-co-glycolic acid) (PLGA) and poly(L-lactic acid) (PLLA), that can release substances such as drugs, proteins and/or active ingredients with a delayed profile. The technology allows the specification of a lag time before the release of substances, thereby enabling the possibility of long-term sustained release by combining batches of spheres with different lag times. In the event that a substance has been completely (or partially) released from a particular batch of spheres, another batch will be ready to commence its release of encapsulated ingredients. The microspheres may also be incorporated into a carrier, such as a hydrogel, a membrane or a scaffold, for ease of implantation at the desired release site.

A particular embodiment of the present invention comprises the following key features:

F1) Core-shell nanocomposite microspheres comprising of poly(D,L-lactic-co-glycolic acid) (PLGA)-rich core and poly(L-lactic acid) (PLLA)-rich shell with the following specifications:
  - a) Weight ratio of PLLA:PLGA within the range of 1:25 to 2:1
  - b) Molecular weight of PLLA greater than 160 kDa
  - c) Molecular weight of PLGA in the range of 7-24 kDa or higher than 75 kDa F2) Controlled release composite comprising encapsulated PLLA/PLGA microspheres in carriers such as hydrogel, membrane and scaffold F3) Method of controlled delivery of an anti-glaucoma drug involving the step of administering a subject the controlled release composite as described in F2

F4) Method of orthopaedic-related treatment comprising the step of in vivo implantation of the PLLA/PLGA microspheres and/or controlled release composite as described in F2

Exemplified in vitro release showed that bupivacaine (30 wt % loading) was released over >14 days. Additionally, the release profile of brimonidine tartarate (BT) using core-shell PLLA/PLGA microspheres with polymer ratio 1:1 (using 100 kDa of PLLA) reported a 4-day lag time (with 7 kDa PLGA) and a 25-day lag time (with 24 kDa PLGA). Suitable carriers include hydrogels such as gelatin-HPA, gelatin-OEGCG, HA-tyramine and HA-OEGCG.

Microsphere compacts (MCs) used for in vivo implantation were sterilized by ethylene oxide. The goats were fasted for 12 h with free access to water prior surgery (to reduce danger of bloat).

Jugular vein catheter, pre-medication and anaesthesia: a permanent catheter was positioned into the jugular vein in order to facilitate blood drawing during the length of the experiment. This same catheter was used to administer premedication and anaesthesia. Premedication was performed with 0.3 mg/kg midazolam (Donnicum, Roche Pharma, Reinach) and 0.2 mg/kg methadone (Methadon Streuli, Streuli Pharma AG, Uznach) intravenously. The anaesthesia was induced with a combination of 3 mg/kg ketamine (Narkan 100; Dr. E Greub AG, Bern) and 1 mg/kg propofol (Propofol 1% Fresenius, Fresenius Kabi, Stans) intravenously. After endotracheal intubation the anaesthetic status was maintained with 1 MAC sevoflurane (2.3% ET) in O2/Air. Preoperative analgesia was assured by the balanced anaesthesia/analgesia protocol: methadone, ketamine. Penicillin was used as a preoperative and postoperative antibiotic treatment.

Operation Field Preparation: the operation field (the goat's left hind limb from the tarsus bone to the middle of the femur) was surgically prepared by clipping the hair using a veterinary hair clipper Aesculap Favorita II 220 Volt (Provet AG, Switzerland) and its replacement blades 1/20 mm, washing and disinfecting the skin with Betadine® (BASF, Switzerland) liquid soap and alcohol. The animal was positioned with a vacuum cushion on a surgical bench in a dorsal decubitus-supine position, the left hind leg in a vertical position distally fixated; the tibia trochlea was in an upright position above the femoral condyle. The surgical field was covered with sterile drapes. An adhesive U-Drape was adhered around the incision; a second adhesive drape was used to cover the rest of the goat.

Surgical approach: a seven to nine cm long medial para-patellar skin incision was performed with a scalpel blade just medial from the insertion point of the adductor magnus longitudinally to the border of the medial femoral condyle and or the patellar ligament, until the insertion of the tendon of the fibularis tertius muscle. The approach was in respect of all anatomical layers (layer by layer). First the skin, then the aponevrosis, then the vastus medialis obliquis portion of the vastus medialis which overlies the superior aspect of the medial-femoral ligament in layer two of the medial stifle joint, then the patellar retinacular fibers of the joint capsule to finally arrive at the level of the joint. The medial aspect of the patella tendon was elongated proximally with a scissors avoiding collaterals of the popliteal arterioles localized more distally. The joint was kept moistened with NaCl 0.9%. The joint and synovial fluid were examined for evidence of unacceptable pathology (osteoarthrosis, synovitis, foreign bodies).

Test item Implantation: bleeding was stopped by cauterisation, before the introduction of the microsphere compacts (MCs). Six goats were implanted with a standardized dose of loaded drug microsphere in the stifle joint and empty loading microsphere were implanted into the stifle joint of another six animals that served as controls. The MCs were implanted into the parapatellar space. The open joint and soft-tissue surfaces was continually rinsed with a sodium chloride 0.9% solution. The intrapatellar fat pad was retracted from the medial femoral condyle and the knee straightened to reduce the patella to avoid inadvertent contact of the soft tissues against the newly prepared defect.

Wound Closure: the infrapatellar fat pad was retracted from the medial femoral condyle and the knee straightened to reduce the patella to avoid inadvertent contact of the soft tissues with the newly implanted MCs. The leg was cycled through a full range of motion. The retinaculum and subcutaneous tissue and joint capsule were closed with Vicryl 2-0, the sub-skin layer was closed with PDS 2-0. The skin was closed with Monocryl 2-0. Finally, the suture was vaporized with Op-Site® spray and a soft bandage was applied.

Post-Operative Care: as soon as possible after the surgery, the animal was disconnected from the anesthesia machine and extubated when swallowing reflexes were fully reestablished. The animal was discharged and returned to its stall, where it was able to tolerate a standing position. At the end of the procedure, after the full recovery of the goat, buprenoprphine hydrochloride (Temgesic®, 10 μg/kg) was administered by intramuscular route. Antibiotic (Penicillin, Ilocillin PS) was administered for 5 days twice daily. For the remainder of the survival period, the goats were kept in one farm environment, and had unrestricted motion until necropsy. A qualified veterinarian examined the animals routinely for any gross abnormalities and signs of excessive discomfort. A gait analysis was performed at 14 days post-operative and just before necropsy.

The present technology is not limited to delivery of hydrophilic/water-soluble substances, as it allows non water-soluble (i.e. not hydrophilic) or minimally soluble drugs and active ingredients to be encapsulated and delivered successfully. For example, dyes such as chlorophenol red (CR), which is not very soluble in water, have been delivered. Another drug which may be delivered using this technology is the anti-fibrotic drug Fluorouracil (5-FU), which is soluble in DMSO/DMF/methanol but not in water.

The aim of encapsulating CR in the microspheres was to determine whether the spheres would break when subjected to friction at the implantation site. In this case, the CR was encapsulated as a solid, which being only minimally water-soluble would not diffuse through the walls of the microspheres, and would only be released when the walls of the microspheres were broken. Upon release, the CR reacts with the surrounding environment and changes color from yellow to violet in the neutral pH of the body fluids. As for 5-FU, it was incorporated into the microspheres in liquid form and also in powder form. In both cases, drug release was measurable.

PLLA should degrade much slower than PLGA in order to retain the shell barrier in the core-shell PLLA-PLGA microspheres during drug release. As the shell was PLLA-rich, once the PLGA degraded, pores would form in the shell so that the drug could be released via diffusion. The time required to degrade PLGA and PLLA was dependent on their molecular weights. Hence, a lower molecular weight PLGA could be combined with a lower molecular weight PLLA without affecting the release profile as long as PLLA would still degrade much slower than PLGA.

Figure 16:
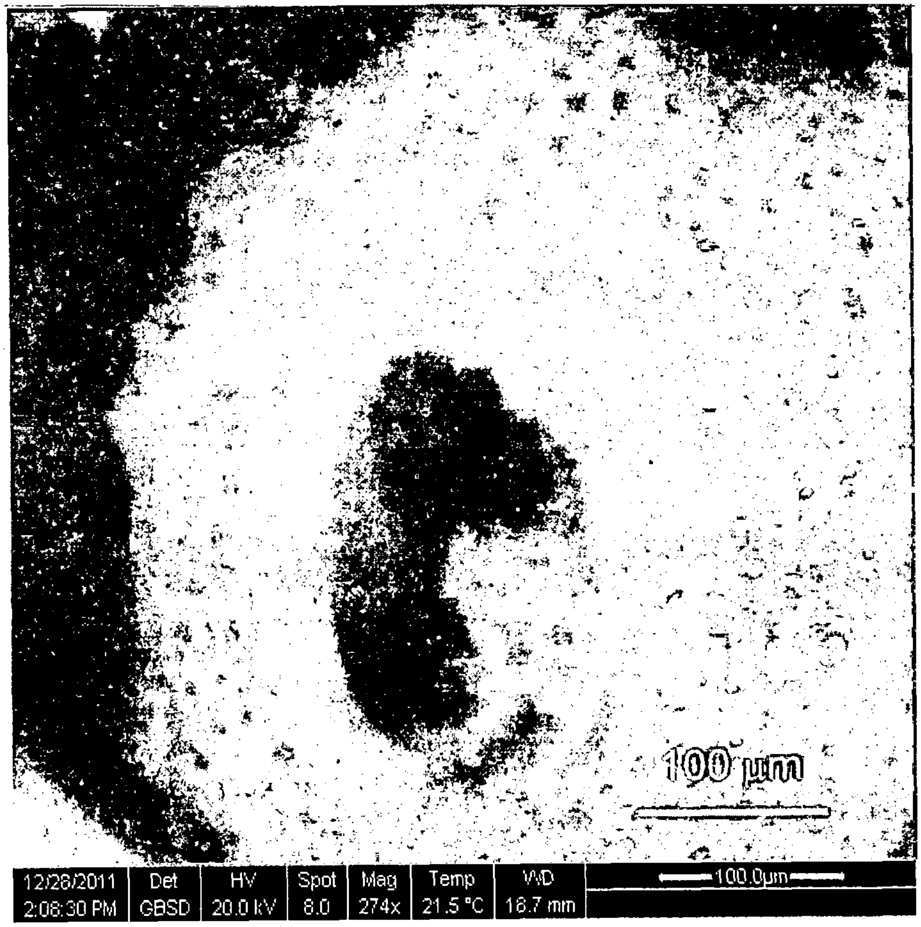
FIG. 16 is a micrograph of a particle according to the present invention after dissolution of the first polymer.

FIG. 16 shows a micrograph of a particle of the invention after degradation of the first polymer. The particle has been broken open to expose the inner structure. Clearly visible are the large hole at the core of the particle and the pores in the surrounding shell, both created by degradation of the first polymer from the particle.

The invention claimed is:

1. A substance comprising a plurality of microparticles, said microparticles comprising:
- a core comprising a first polymer; and
- a shell surrounding said core and comprising the first polymer and a second polymer, said second polymer being less rapidly degradable than the first polymer, wherein the first polymer forms a plurality of continuous pathways through the shell.

2. The substance of claim 1 wherein the second polymer is less rapidly biodegradable than the first polymer.

3. The substance of claim 1 wherein the second polymer is semicrystalline.

4. The substance of claim 1 wherein the first polymer is poly(D,L-lactic-co-glycolic acid) (PLGA) and the second polymer is poly(L-lactic acid) (PLLA).

5. The substance of claim 1 wherein the first polymer is present in the shell at less than about 25 wt %.

6. The substance of claim 1 wherein the core comprises a releasable material.

7. The substance of claim 6 wherein the releasable material is in particulate form or is adsorbed onto, or absorbed into, or both adsorbed onto and absorbed into, nanoparticles in the core.

8. The substance of claim 7 wherein the first and second polymers are substantially immiscible and wherein the nanoparticles or the particles of the releasable material, are smaller than the diameter of the pathways.

9. The substance of claim 6 wherein the releasable material is selected from the group consisting of a protein, a protein fragment, an enzyme, DNA, a DNA fragment, RNA, an RNA fragment, a polysaccharide, a hormone, a growth factor, a drug which is none of the above and mixtures of any two or more of these.

10. The substance of claim 1 wherein the microparticles are dispersed in a hydrogel, a membrane or a scaffold or at least partially adhered together to form a solid mass.

11. The substance of claim 1, in combination with a second substance according to claim 1, wherein:
- the cores of the microparticles of each of the substances comprise a releasable material; and
- the shells of the microparticles of the different substances are such that they degrade over different times under the same conditions, whereby the releasable materials of the microparticles of the different substances are capable of releasing sequentially.

12. A process for making a substance comprising a plurality of microparticles, said process comprising:
- combining a first solution comprising a first polymer in a first solvent, and a second solution comprising a second polymer in a second solvent, to form a mixed polymer solution, said second polymer being less rapidly degradable than the first polymer and the first and second polymers being at least partially immiscible, optionally substantially immiscible, and said first and second solvents being miscible with each other;

emulsifying the mixed polymer solution in an aqueous medium to form an emulsion, said aqueous medium being at least partially immiscible with the first and second solvents, wherein the aqueous medium is at least partially saturated with the first solvent and/or the second solvent;

aging the emulsion for sufficient time to allow for at least partial separation of the first polymer and the second polymer within droplets of the emulsion so as to form a core comprising the first polymer and a shell surrounding the core and comprising the first polymer and the second polymer; and removing the first and second solvents to form the substance as an aqueous suspension, wherein the microparticles each comprise a core comprising the first polymer and a shell surrounding said core and comprising the first polymer and the second polymer, wherein the first polymer forms a plurality of continuous pathways through the shell.

13. The process of claim 12 wherein the first solution comprises a releasable material, whereby the cores of the microparticles contain said releasable material.

14. The process of claim 12 wherein the step of aging is conducted with continuous stirring.

15. The process of claim 12 wherein the step of removing the first and second solvents is conducted at least partially concurrently with the step of aging whereby the steps of aging and removing the first and second solvents are for sufficient time to allow for at least partial separation of the first polymer and the second polymer within droplets of the emulsion so as to form a core comprising the first polymer and a shell surrounding the core and comprising the first polymer and the second polymer, wherein the first polymer forms a plurality of continuous pathways through the shell.

16. The process of claim 12 wherein the first and second solvents are partially miscible with the aqueous medium and the step of removing the first and second solvents comprises diluting the emulsion with the aqueous medium which has neither the first nor the second solvent therein.

17. The process of claim 12 comprising separating the particulate substance from the aqueous medium and heating the separated particulate substance in a mold for sufficient time and at sufficient temperature to cause the microparticles to adhere together so as to form pellets of the particulate substance.

18. The process of claim 17 wherein the first solution comprises a releasable material and the sufficient temperature is at or above the glass transition temperature of the second polymer and below the temperature at which said releasable material degrades over the sufficient time.

19. A method for delivering a material to a liquid comprising exposing a substance according to claim 1 to said liquid in the presence of a degrading agent which is capable of degrading the first polymer, said substance being one in which the cores of the microparticles contain the material.

20. The method of claim 19 wherein the microparticles of the substance are adhered together.

* * * * *